United States Patent
Desai et al.

(10) Patent No.: US 12,220,678 B2
(45) Date of Patent: *Feb. 11, 2025

(54) PADDLE CONFIGURATION FOR A PARTICLE COATING REACTOR

(71) Applicant: Applied Materials, Inc, Santa Clara, CA (US)

(72) Inventors: Govindraj Desai, Karnataka (IN); Sekar Krishnasamy, Bangalore (IN); Sumedh Acharya, Bangalore (IN); Dakshalkumar Patel, Gujarat (IN); Jonathan Frankel, Los Gatos, CA (US); Quoc Truong, San Ramon, CA (US); Mario Cambron, San Jose, CA (US); Ravindra Patil, Santa Clara, CA (US)

(73) Assignee: Applied Materials, Inc., Santa Clara, CA (US)

( * ) Notice: Subject to any disclaimer, the term of this patent is extended or adjusted under 35 U.S.C. 154(b) by 531 days.

This patent is subject to a terminal disclaimer.

(21) Appl. No.: 17/073,111

(22) Filed: Oct. 16, 2020

(65) Prior Publication Data

US 2022/0032258 A1    Feb. 3, 2022

(30) Foreign Application Priority Data

Jul. 30, 2020  (IN) .............................. 202041032720

(51) Int. Cl.
  *C23C 16/44*    (2006.01)
  *B01J 8/00*    (2006.01)
  (Continued)

(52) U.S. Cl.
  CPC ......... *B01J 19/0066* (2013.01); *B01J 8/0045* (2013.01); *B05C 19/008* (2013.01);
  (Continued)

(58) Field of Classification Search
  None
  See application file for complete search history.

(56) References Cited

U.S. PATENT DOCUMENTS 3,818,982 A    6/1974   Wagner
3,946,996 A    3/1976   Gergely
    (Continued)

FOREIGN PATENT DOCUMENTS

CN    103160795    6/2013
CN    202962569    6/2013
    (Continued)

OTHER PUBLICATIONS

Office Action in Taiwanese Appln. No. 110127642, dated Apr. 12, 2022, 6 pages (with English search report).
(Continued)

*Primary Examiner* — Karla A Moore
(74) *Attorney, Agent, or Firm* — Fish & Richardson P.C.

(57) ABSTRACT

A reactor for coating particles includes a stationary vacuum chamber to hold a bed of particles to be coated, a chemical delivery system, and a paddle assembly. The paddle assembly includes a rotatable drive shaft and a first plurality of paddles and a second plurality of paddles that extend radially from the drive shaft. The spacing, cross-sections, and oblique angles of the paddles are such that orbiting of the paddles causes the first plurality of paddles and the second plurality of paddles to displace substantially equal volumes in opposite directions in the lower portion of the stationary vacuum chamber.

17 Claims, 11 Drawing Sheets

(51) Int. Cl.
   *B01J 19/00* (2006.01)
   *B05C 19/00* (2006.01)
   *B05C 19/02* (2006.01)
   *B05D 1/00* (2006.01)

(52) U.S. Cl.
   CPC .............. *B05C 19/02* (2013.01); *B05D 1/60* (2013.01); *C23C 16/4417* (2013.01); *B01J 8/0025* (2013.01)

(56) References Cited

U.S. PATENT DOCUMENTS

| | | | |
|---|---|---|---|
| 5,744,555 | A | 4/1998 | Ames et al. |
| 6,613,383 | B1 | 9/2003 | George et al. |
| 9,951,419 | B2 | 4/2018 | Jiang et al. |
| 11,299,806 | B2* | 4/2022 | Frankel ............... B01F 27/051 |
| 11,674,223 | B2* | 6/2023 | Frankel ............. C23C 16/45555 366/343 |
| 11,692,265 | B2* | 7/2023 | Frankel ............... C23C 16/442 427/212 |
| 11,717,800 | B2* | 8/2023 | Frankel ............... B01F 27/112 118/716 |
| 2003/0175186 | A1 | 9/2003 | Cohen |
| 2004/0256326 | A1 | 12/2004 | Hannon et al. |
| 2008/0131570 | A1 | 6/2008 | Bokelmann et al. |
| 2008/0159068 | A1* | 7/2008 | Kato ........................ A21C 1/06 366/325.92 |
| 2008/0254219 | A1 | 10/2008 | Koh et al. |
| 2009/0011293 | A1 | 1/2009 | Wood et al. |
| 2011/0116984 | A1 | 5/2011 | Rehmat et al. |
| 2011/0152070 | A1 | 6/2011 | Fansler |
| 2011/0200822 | A1 | 8/2011 | Detavernier et al. |
| 2012/0009343 | A1 | 1/2012 | Van Ommen |
| 2013/0059073 | A1 | 3/2013 | Jiang et al. |
| 2014/0127756 | A1 | 5/2014 | Bolz et al. |
| 2015/0125599 | A1 | 5/2015 | Lindfors et al. |
| 2015/0250731 | A1 | 9/2015 | Hoppu et al. |
| 2016/0166997 | A1 | 2/2016 | Rass et al. |
| 2017/0007545 | A1 | 1/2017 | Hoppu et al. |
| 2017/0282136 | A1 | 10/2017 | Nielsen et al. |
| 2017/0333359 | A1 | 11/2017 | Goldstein |
| 2018/0221294 | A1 | 8/2018 | Carlsson et al. |
| 2018/0363136 | A1 | 12/2018 | Spencer, II et al. |
| 2019/0062914 | A1 | 2/2019 | King et al. |
| 2019/0099328 | A1 | 4/2019 | Zhu et al. |
| 2019/0126314 | A1 | 5/2019 | Monastiriotis et al. |
| 2019/0376181 | A1 | 12/2019 | Neikirk et al. |
| 2019/0376182 | A1 | 12/2019 | Neikirk et al. |
| 2020/0185760 | A1 | 6/2020 | Ho et al. |
| 2020/0240013 | A1* | 7/2020 | Geertsen ................... B01J 2/16 |
| 2020/0338517 | A1 | 10/2020 | Frankel et al. |
| 2020/0340108 | A1 | 10/2020 | Frankel et al. |
| 2022/0032258 | A1* | 2/2022 | Desai ........................ B01J 2/10 |
| 2022/0205091 | A1* | 6/2022 | Frankel ................ B01J 19/0066 |
| 2023/0279543 | A1* | 9/2023 | Frankel ............... C23C 16/4417 366/343 |
| 2023/0313368 | A1* | 10/2023 | Frankel ................ C23C 16/442 427/70 |
| 2023/0347310 | A1* | 11/2023 | Frankel ............. C23C 16/45555 |

FOREIGN PATENT DOCUMENTS

| | | |
|---|---|---|
| CN | 203590584 | 5/2014 |
| CN | 203648529 | 6/2014 |
| CN | 203886533 | 10/2014 |
| CN | 105648422 | 6/2016 |
| CN | 205667839 | 11/2016 |
| CN | 106635788 | 5/2017 |
| CN | 106994460 | 8/2017 |
| CN | 107029576 | 8/2017 |
| CN | 107335363 | 11/2017 |
| CN | 206715767 | 12/2017 |
| CN | 207310255 | 5/2018 |
| CN | 207342562 | 5/2018 |
| CN | 207680508 | 8/2018 |
| CN | 111068603 | 4/2020 |
| JP | H 04-180825 | 6/1992 |
| JP | 2005-270955 | 10/2005 |
| JP | 2006-016661 | 1/2006 |
| JP | 2008-007768 | 1/2008 |
| JP | 2008-083199 | 4/2008 |
| KR | 10-2017-0069968 | 6/2017 |
| KR | 10-1868703 | 6/2018 |
| TW | 200803030 | 1/2008 |
| TW | 201329113 | 7/2013 |
| TW | 201832399 | 9/2018 |
| WO | WO 01/37795 | 5/2001 |
| WO | WO 2007/049873 | 5/2007 |
| WO | WO 2007/123510 | 11/2007 |
| WO | WO 2014/044907 | 3/2014 |
| WO | WO 2019/040857 | 2/2019 |

OTHER PUBLICATIONS

International Search Report and Written Opinion in International Appln. No. PCT/US2021/043734, dated Nov. 24, 2021, 9 pages.

Didden et al., "Fluidized-bed atomic layer deposition reactor for the synthesis of core-shell nanoparticles" Review of Scientific Instruments, 2014, 85:013905-1-8.

King et al., "Atomic layer deposition on particles using a fluidized bed reactor with in situ mass spectrometry," Surface & Coatings Technology, 2007, 201(22-23):9163-71.

PCT International Search Report and Written Opinion in International Appln. No. PCT/US2020/029372, dated Jul. 31, 2020, 13 pages.

TW Office Action in Taiwanese Appln. No. 109113246, dated Nov. 19, 2020, 6 pages (with English search report).

* cited by examiner

PADDLE CONFIGURATION FOR A PARTICLE COATING REACTOR

TECHNICAL FIELD

This disclosure pertains coating particles, e.g., particles that include active pharmaceutical ingredients, with thin organic and inorganic films.

BACKGROUND

It is of great interest to the pharmaceutical industry to develop improved formulations of active pharmaceutical ingredients (API). Formulation can influence the stability and bioavailability of the API as well as other characteristics. Formulation can also influence various aspects of drug product (DP) manufacture, for example, ease and safety of the manufacturing process.

Numerous techniques for encapsulating or coating API have been developed. Some existing techniques for the coating of API include spray coating, plasma polymerization, hot wire chemical vapor deposition (CVD), and rotary reactors. Spray coating is an industrially scalable technique that has been widely adopted by the pharmaceutical industry. However, coating non-uniformities (both within particle and from particle to particle) prevent the use of these techniques for improving the delivery profile or stability of active pharmaceutical ingredients (APIs). Particle agglomeration during spray coating also causes significant challenges. Meanwhile, techniques such as plasma polymerization are difficult to scale, applicable only to certain precursor chemistries, and can result in the degradation of sensitive APIs. Existing hot-wire CVD processes utilizing hot wire radical sources inside the reaction vessel are poorly scalable and are not suitable for thermally sensitive APIs. Rotary reactors include atomic layer deposition (ALD) and initiated CVD (iCVD) reactors. However, ALD reactors are suitable for inorganic coatings and not for organic polymer coatings, and existing iCVD designs do not adequately prevent API degradation and are not scalable for high volume manufacturing. Other techniques include polymer mesh coating, pan coating, aerosolized coating, and fluidized bed reactor coating.

SUMMARY

A reactor for coating particles includes a stationary vacuum chamber to hold a bed of particles to be coated with the chamber having a lower portion that forms a half-cylinder and an upper portion, a vacuum port in the upper portion of the chamber, a chemical delivery system including a gas injection assembly to a deliver a precursor or reactant gas and a purge gas into the lower portion of the chamber, and a paddle assembly. The paddle assembly includes a rotatable drive shaft extending through the chamber along the axial axis of the half cylinder and a plurality of paddles extending radially from the drive shaft such that the rotation of the drive shaft by a motor orbits the plurality of paddles about the drive shaft. The plurality of paddles include a first plurality of outer paddles and a second plurality of inner paddles. The first plurality of outer paddles have a first cross-section including an outer curvature and are oriented at a first oblique angle, and the second plurality of inner paddles have a second cross-section and are oriented at a second oblique angle.

In one aspect, the first cross-section and second cross-section and first oblique angle and second oblique angle are such that orbiting of the paddles causes the first plurality of paddles and the second plurality of paddles to displace substantially equal volumes in the lower portion of the stationary vacuum chamber.

In another aspect, the outer curvature of the first cross-section matches an inner curvature of the lower portion of the stationary vacuum chamber. The outer curvature of the first cross-section can be parabolic.

In another aspect, a spacing between the outer curvature of the multiple outer paddles and the inner curvature of the lower portion of the stationary vacuum chamber is less than 1.5 millimeters.

In another aspect, where the multiple inner paddles are positioned and oriented such that orbiting of the multiple inner paddles results in no dead zone in the powder volume in the lower portion of the stationary vacuum chamber.

In another aspect, a number of inner paddles of the multiple inner paddles and the second cross-section of each inner paddle results in dead zones in the powder volume of less than 5% of the lower portion of the station vacuum chamber when the multiple inner paddles orbit about the shaft axis.

In another aspect, the first set of multiple outer paddles oriented at the first oblique angle drives particles in a first direction along the axial axis and the second set of multiple inner paddles oriented at the second oblique angle drives particles in a second direction along the axial axis opposite to the first direction.

In another aspect, the first oblique angle and the second oblique angle and the first cross-section and second cross-section are each displace a same volume in the lower portion of the stationary vacuum chamber when the multiple inner paddles and multiple outer paddles orbit about the drive shaft.

In another aspect, the first oblique angle and the first cross-section, and the second oblique angle and the second cross-section of the multiple inner paddles and multiple outer paddles, respectfully, results in no scooping action of the respective blades and the powder when the multiple paddles orbit about the drive shaft.

In another aspect, the first oblique angle and the first cross-section, and the second oblique angle and the second cross-section of the multiple inner paddles and multiple outer paddles, respectfully results in a bed surface angle of powder with respect to an initial powder level of less than 2 degrees after a rotation of the drive shaft about the axial axis.

In another aspect, at least a first portion of a first cross-sectional area of each of the multiple outer paddles overlaps with at least a second portion of a second cross-sectional area of each of the multiple inner paddles along the shaft axis.

In another aspect, a third portion of each outer blade of the multiple outer blades overlaps with a fourth portion of another outer blade perpendicular to the drive shaft axis. A fifth portion of each inner blade of the multiple inner blades can overlap with a sixth portion of another inner blade perpendicular to the drive shaft axis.

In another aspect, a reactor for coating particles includes a stationary vacuum chamber to hold a bed of particles to be coated, the chamber having a lower portion that forms a half-cylinder and an upper portion, a vacuum port in the upper portion of the chamber, a chemical delivery system including a gas injection assembly to a deliver a precursor or reactant gas and a purge gas into the lower portion of the chamber, and a paddle assembly. The paddle assembly includes a rotatable drive shaft extending through the chamber along the axial axis of the half cylinder, multiple paddles, including a first set of multiple outer paddles and a second set of multiple inner paddles, extending radially from the drive shaft such that the rotation of the drive shaft by a motor orbits the multiple paddles about the drive shaft.

In another aspect, the first set of multiple outer paddles includes a first cross-section including an outer curvature and oriented at a first oblique angle, the second set of multiple inner paddles includes a second cross-section and oriented at a second oblique angle.

In another aspect, the first cross-section and second cross-section and first oblique angle and second oblique angle and a spacing of paddles about the drive shaft substantially eliminates a dead zone from the lower portion of the chamber.

In another aspect, the multiple paddles are positioned and oriented such that orbiting of the multiple paddles results in a dead zone in the lower portion of the chamber, e.g., of less than 5% of the lower portion, of less than 3% of the lower portion, of less than 1% of the lower portion.

In one aspect, a method of coating particles includes dispensing particles into a vacuum chamber to fill at least a lower portion of the chamber that forms a half-cylinder, evacuating the chamber through a vacuum port in an upper portion of the chamber, rotating a paddle assembly such that multiple paddles orbit a drive shaft at a first rotational speed, and injecting a reactant or precursor gas into the lower portion of the chamber at a second flow rate and third gas pressure as the paddle assembly rotates at the first rotational speed.

In another aspect, a gas residence time of the injected reactant or precursor gas within a particle bed of the dispense particles is a function of the first rotational speed, second flow rate, and third gas pressure.

Implementations may include, but are not limited to, one or more of the following possible advantages. Particles, e.g., API particles, can be coated with an organic or inorganic layer in a high volume manufacturing process, thereby providing lower cost of manufacturing and reduced drug product prices. Particles can be coated with a thin layers, thus providing a drug product with an advantageous volume fraction of API. In addition, the process can result in layer(s) encapsulating the API that are uniform within a particle and from particle-to-particle, providing more consistent properties to the drug formulations. The processes described can result in improved throughput and reduced cycle time due to the convective-type mixing. Additionally, the configurations described can result in improved ease of unloading particles and increased yield, e.g., retrieving at least 99% of the powder from the chamber post-process. Improved de-agglomeration of the particles, e.g., such that the paddle assembly may break up clumps of the powder prior to coating can additionally result from the processes described herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting.

Other features and advantages of the invention will be apparent from the following detailed description and figures, and from the claims.

BRIEF DESCRIPTION OF THE DRAWINGS

FIG. 2 can be taken along line 2-2 in FIG. 1.

FIG. 3B can be taken along line 3B-3B in FIG. 3A.

FIG. 3D can be taken along line 3D-3D in FIG. 3C.

FIG. 7 can be taken along line 7-7 in FIG. 4.

FIG. 8 can be taken along line 8-8 in FIG. 1.

Like reference numbers and designations in the various drawings indicate like elements.

DETAILED DESCRIPTION

Figure 1:
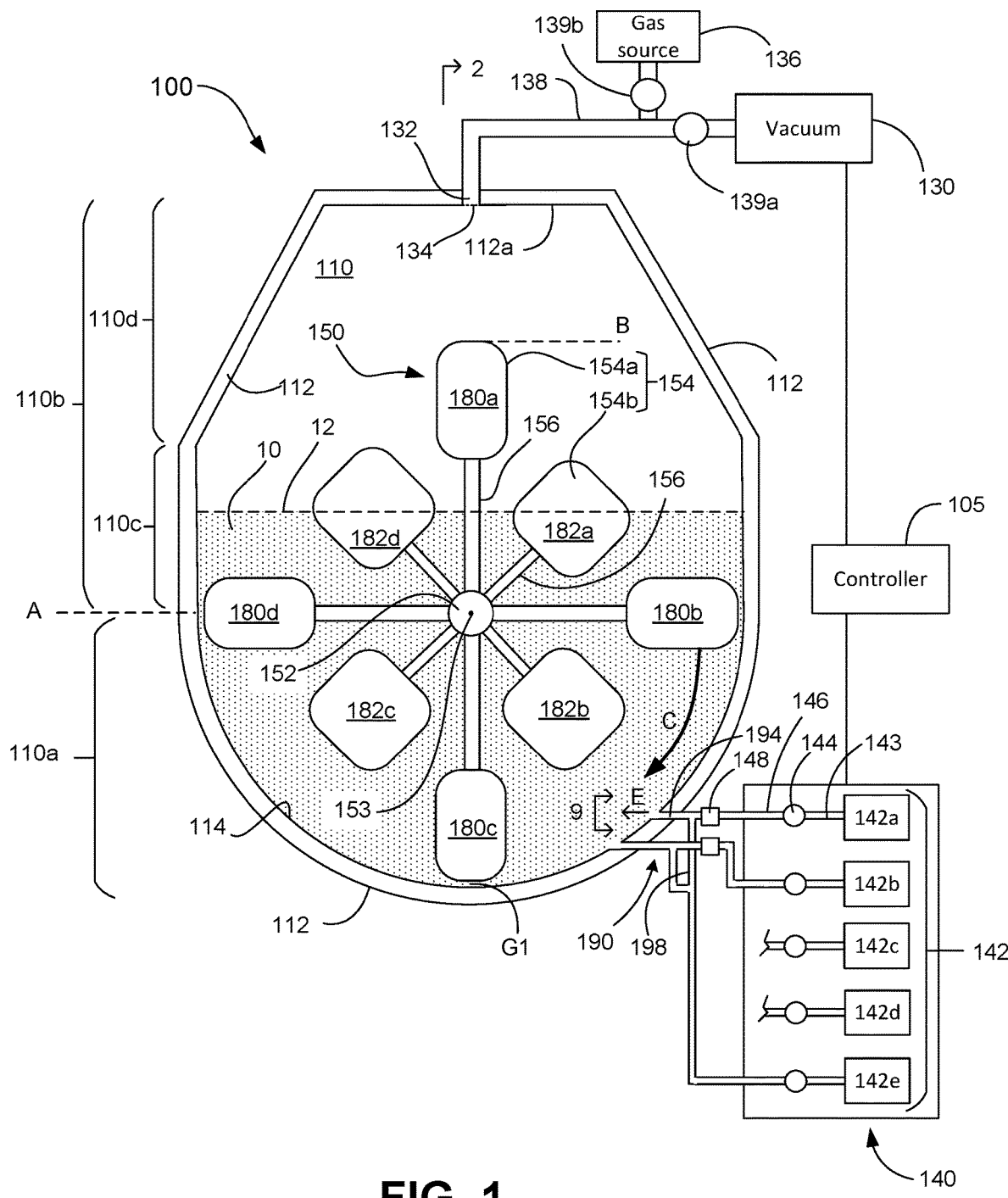
FIG. 1 is a schematic front view of a reactor for ALD and/or CVD coating of particles, e.g., drugs, that includes a stationary drum.

There are various methods for encapsulating API particles. In many cases, these methods result in a coating that is relatively thick. While such coatings can impart desirable properties, the high ratio of coating to API can make it difficult to create a drug product in which the volume fraction of API is as high as desired. In addition, the coating encapsulating the API can be non-uniform, making it difficult to provide formulations with consistent properties. Furthermore, coating techniques that can provide satisfactory consistency have not be scalable for industrial manufacturing.

An approach that may address these issues is to use a stationary "drum" in which particles are agitated by rotating paddles, and process gas is injected into the drum through the drum sidewall. This can force the process gas to percolate through the particle bed, which can improve uniformity of coating across the particles.

Another issue is that particles tend to agglomerate in the reaction chamber. As a result, process gas might not coat the regions where the particles contact, leading to non-uniform coating. Although stirring the particle bed with paddles can prevent some agglomeration, the particles can still tend to form micro-aggregates, e.g., clumps of up to 10× the primary particle size. In some techniques, the particles are removed from the reactor to perform de-aggregation. However, removal of the particles can significantly impact throughput, and can provide an opportunity for contamination or spillage.

An approach that may address this issue is to select paddle shape and orientation on the drive shaft such that, when the paddle assembly including the selected paddles orbit the drive shaft, the paddle assembly generates convective motion between an inner volume and an outer volume of particles (also referred to as a powder) displaced in the particle bed, resulting in de-agglomeration of the particles. Moreover, paddle shape and orientation can be selected to avoid "dead zones" in the particle bed.

The particles treated using the apparatus and methods discussed below can have an average particle size (D50) in the 1-100 μm, e.g., 1-30 μm, e.g., 1-10 μm range, although nano-scale particles are also possible. The particles can include both API and an excipient, or the particles can consist of API.

Drug

The term "drug," in its broadest sense includes all small molecule (e.g., non-biologic) APIs. The drug could be selected from the group consisting of an analgesic, an anesthetic, an anti-inflammatory agent, an anthelmintic, an anti-arrhythmic agent, an antiasthma agent, an antibiotic, an anticancer agent, an anticoagulant, an antidepressant, an antidiabetic agent, an antiepileptic, an antihistamine, an antitussive, an antihypertensive agent, an antimuscarinic agent, an antimycobacterial agent, an antineoplastic agent, an antioxidant agent, an antipyretic, an immunosuppressant, an immunostimulant, an antithyroid agent, an antiviral agent, an anxiolytic sedative, a hypnotic, a neuroleptic, an astringent, a bacteriostatic agent, a beta-adrenoceptor blocking agent, a blood product, a blood substitute, a bronchodilator, a buffering agent, a cardiac inotropic agent, a chemotherapeutic, a contrast media, a corticosteroid, a cough suppressant, an expectorant, a mucolytic, a diuretic, a dopaminergic, an antiparkinsonian agent, a free radical scavenging agent, a growth factor, a haemostatic, an immunological agent, a lipid regulating agent, a muscle relaxant, a parasympathomimetic, a parathyroid calcitonin, a biphosphonate, a prostaglandin, a radio-pharmaceutical, a hormone, a sex hormone, an anti-allergic agent, an appetite stimulant, an anoretic, a steroid, a sympathomimetic, a thyroid agent, a vaccine, a vasodilator and a xanthine.

Exemplary types of small molecule drugs include, but are not limited to, acetaminophen, clarithromycin, azithromycin, ibuprofen, fluticasone propionate, salmeterol, pazopanib HCl, palbociclib, and amoxicillin potassium clavulanate.

Pharmaceutically Acceptable Excipients, Diluents, and Carriers

Pharmaceutically acceptable excipients include, but are not limited to:
(1) surfactants and polymers including: polyethylene glycol (PEG), polyvinylpyrrolidone (PVP), sodium lauryl sulfate, polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropylmethyl cellulose phthalate, polyacrylates and polymethacrylates, urea, sugars, polyols, carbomer and their polymers, emulsifiers, sugar gum, starch, organic acids and their salts, vinyl pyrrolidone and vinyl acetate;
(2) binding agents such as cellulose, cross-linked polyvinylpyrrolidone, microcrystalline cellulose;
(3) filling agents such as lactose monohydrate, lactose anhydrous, microcrystalline cellulose and various starches;
(4) lubricating agents such as agents that act on the flowability of a powder to be compressed, including colloidal silicon dioxide, talc, stearic acid, magnesium stearate, calcium stearate, silica gel;
(5) sweeteners such as any natural or artificial sweetener including sucrose, xylitol, sodium saccharin, cyclamate, aspartame, and acesulfame K;
(6) flavoring agents;
(7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quarternary compounds such as benzalkonium chloride;
(8) buffers;
(9) Diluents such as pharmaceutically acceptable inert fillers, such as microcrystalline cellulose, lactose, dibasic calcium phosphate, saccharides, and/or mixtures of any of the foregoing;
(10) wetting agents such as corn starch, potato starch, maize starch, and modified starches, and mixtures thereof;
(11) disintegrants; such as croscarmellose sodium, crospovidone, sodium starch glycolate; and
(12) effervescent agents such as effervescent couples such as an organic acid (e.g., citric, tartaric, malic, fumaric, adipic, succinic, and alginic acids and anhydrides and acid salts), or a carbonate (e.g., sodium carbonate, potassium carbonate, magnesium carbonate, sodium glycine carbonate, L-lysine carbonate, and arginine carbonate) or bicarbonate (e.g. sodium bicarbonate or potassium bicarbonate)

Metal Oxide Material

The term "metal oxide material," in its broadest sense includes all materials formed from the reaction of elements considered metals with oxygen-based oxidants. Exemplary metal oxide materials include, but are not limited to, aluminum oxide, titanium dioxide, iron oxide, gallium oxide, magnesium oxide, zinc oxide, niobium oxide, hafnium oxide, tantalum oxide, lanthanum oxide, and zirconium dioxide. Exemplary oxidants include, but are not limited to, water, ozone, and inorganic peroxide.

Atomic Layer Deposition (ALD)

Atomic layer deposition is a thin film deposition technique in which the sequential addition of self-limiting monolayers of an element or compound allows deposition of a film with thickness and uniformity controlled to the level of an atomic or molecular monolayer. Self-limited means that only a single atomic layer is formed at a time, and a subsequent process step is required to regenerate the surface and allow further deposition.

Molecular Layer Deposition (MLD)

Molecular layer deposition is analogous to atomic layer deposition but using organic precursors and forming organic thin films. During a typical MLD process two homo-bifunctional precursors are used. A first precursor is introduced into a chamber. The molecules of the first precursor react with reactive groups on the substrate surface via the corresponding linking chemistry to add a molecular layer of the first precursor on the substrate surface with new reactive sites. After purging, a second precursor is introduced and the molecules of the second precursor react with the new reactive sites provided by the first precursor generating a molecular layer of the first precursor linked to the second precursor. This is followed by another purge cycle.

Reactor System

Figure 2:
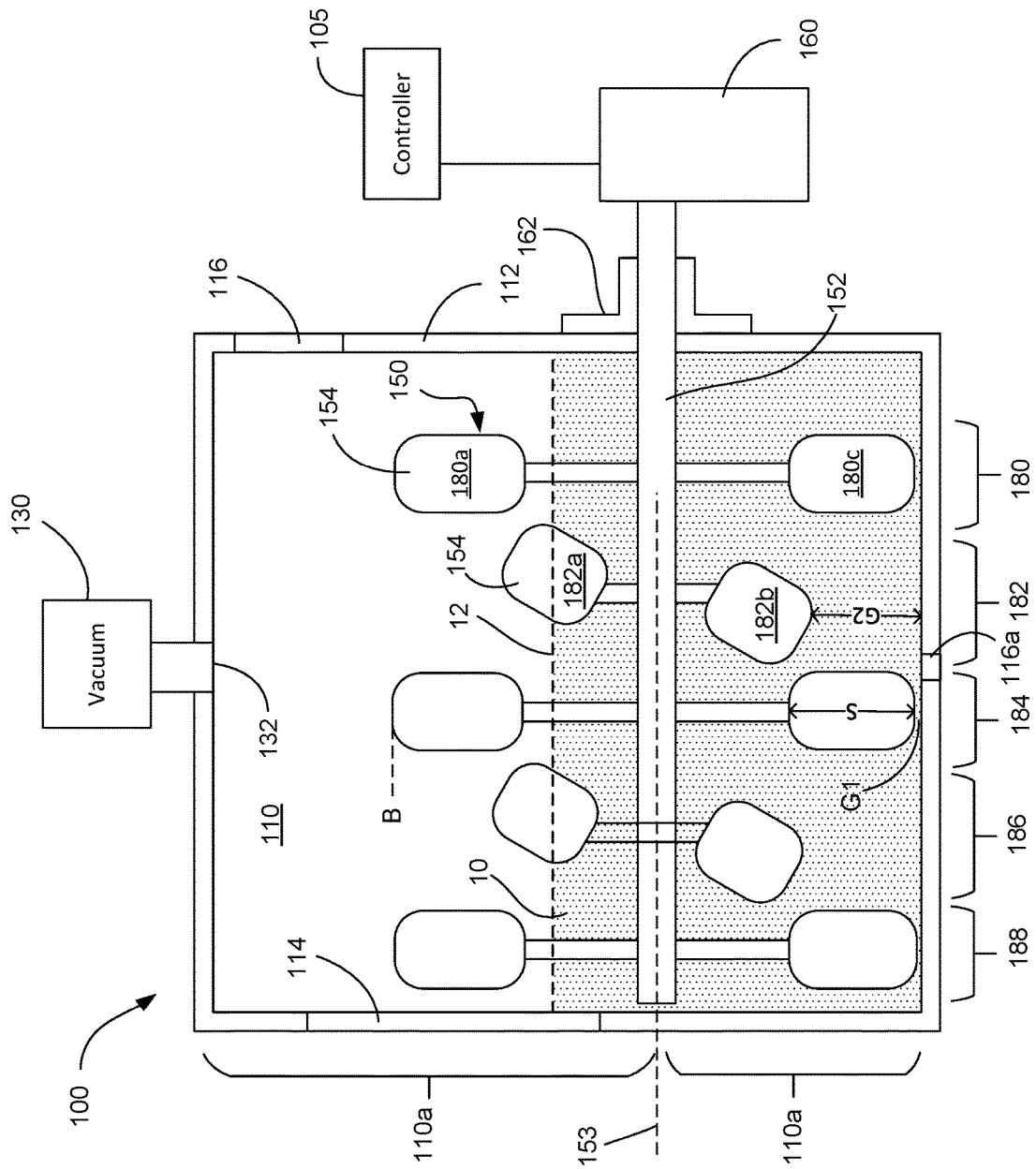
FIG. 2 is a schematic side view of the reactor of FIG. 1.

FIGS. 1-2 illustrate a reactor system 100 for coating particles with a thin-film coating. The reactor system 100 can perform the coating using ALD and/or MLD coating conditions. The reactor system 100 permits a deposition process (ALD or MLD), to be performed at higher (above 50° C., e.g., 50-100° C.) or lower processing temperature, e.g., below 50° C., e.g., at or below 35° C. For example, the reactor system 100 can form thin-film oxides on the particles primarily by ALD at temperatures of 22-35° C., e.g., 25-35° C., 25-30° C., or 30-35° C. In general, the particles can remain or be maintained at such temperatures. This can be achieved by having the reactant gases and/or the interior surfaces of the reactor chamber remain or be maintained at such temperatures.

The reactor system 100 includes a stationary vacuum chamber 110 that encloses a paddle assembly 150.

The vacuum chamber 110 is enclosed by chamber walls 112. A lower portion 110a of the chamber 110 forms a half-cylinder with a semicircular cross-section (as viewed along the central axis of the half-cylinder). The cross-section (again, as viewed along the central axis of the half-cylinder) of the upper portion 110b can be uniform along the length of the chamber 110 (the length is along the central axis of the half-cylinder). This can help ensure uniform gas flow along the length of the chamber. If gas flow is sufficiently uniform, the cross section can be non-uniform, e.g., narrowing toward the top when viewed horizontal but perpendicular to the central axis of the half-cylinder) to reduce the volume of the chamber 110.

The cross-section of the upper portion 110b can otherwise be selected to conserve space in the fabrication facility while still enclosing the paddle assembly 150. For example, the upper portion 110b of the chamber 110 can be a rectangular solid (see FIG. 6A), a half-cylinder with a semicircular cross-section, or other appropriate shape that does not block rotation of the paddle assembly 150. In some implementations, the upper portion 110b of the chamber has a lower section 110c that is adjacent the lower portion 110a and that has vertical side walls, e.g., a rectangular solid volume. An upper section 110c that extends between the lower section 110c and a ceiling 112a of the chamber 110 can have a cross-section (again, as viewed along the central axis of the half-cylinder) that is triangular or trapezoidal.

Figure 6B:
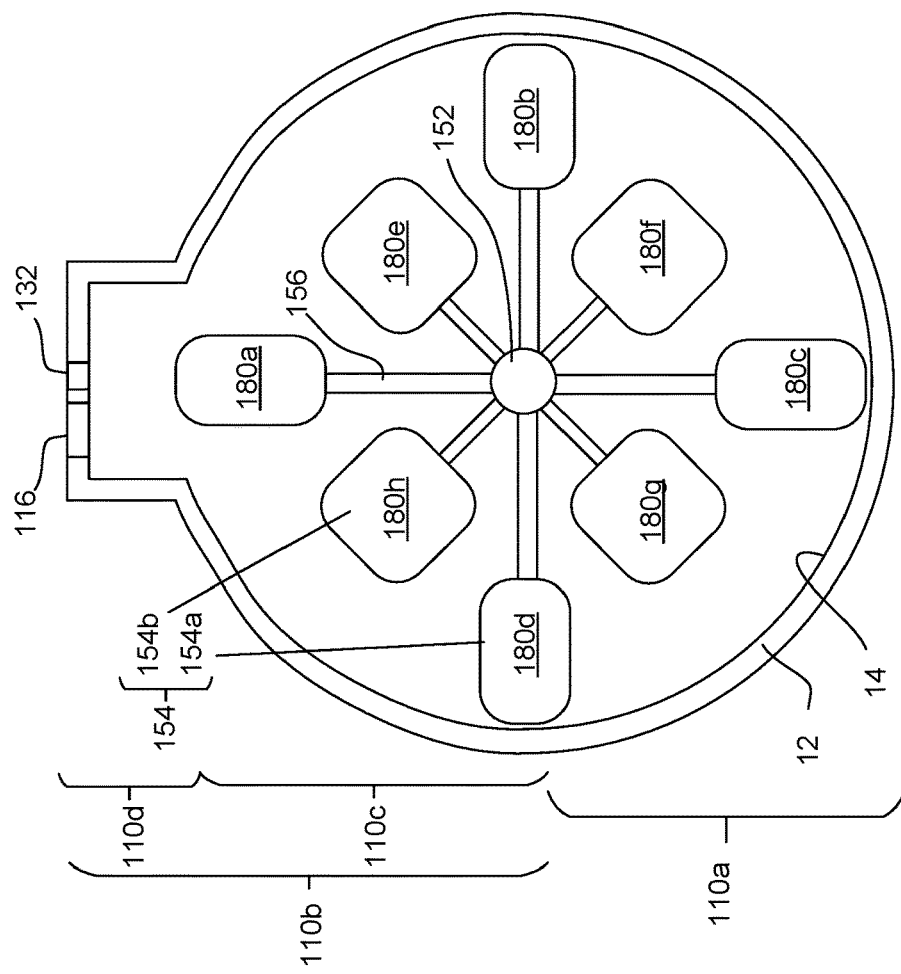
FIG. 6B is a schematic front view of yet another implementation of a group of paddles from a paddle assembly.

In some implementations, e.g., as shown in FIG. 6B (but which could be combined with other paddle assemblies), the curved portion of the chamber wall along the lower section 110c of the upper chamber 110b. An upper section 110d that extends between the lower section 110c and a ceiling 112a of the chamber 110 can provide a volume for a vacuum port 132 and/or a powder delivery port 116. This configuration can avoid powder build up, e.g., caused by the paddle assembly throwing the powder, along a portion of the side wall 12 that is out of reach of the paddles 154.

The chamber walls 110 can be a material, e.g., stainless steel, that is inert to the deposition process, and/or the interior surfaces of the chamber walls 110 can be coated with a material that is inert to the deposition process. In some implementations, a viewing port 114 of transparent material, e.g., quartz, can be formed through the chamber wall 112 to permit an operator to view an interior of the chamber 110.

In operation, the chamber 110 is partially filled by particles, e.g., API-containing particles, that provide a particle bed 10. For superior throughput, the particle bed 10 fills at least the lower portion 110a of the chamber, e.g., the top surface 12 of the particle bed 10 is at or above the lower portion 110a (indicated at A). On the other hand, the top surface 12 of the particle bed 10 should be below the top (indicated at B) of the paddle assembly 150 to avoid poor mixing of the particle bed. The chamber walls 112 can include one or more sealable ports 116 to permit the particles to be placed into and removed from the chamber 110.

The chamber 110 is coupled to a vacuum source 130. The port 132 through the chamber wall 112 to connect the vacuum source 130 to the chamber can be located in the upper portion 110b of the chamber 110. In particular, the port 132 can be located above the expected position of the top surface 12 of the particle bed, e.g., above the top (indicated at B) of the paddle assembly 150, e.g., in the chamber ceiling.

The vacuum source 130 can be an industrial vacuum pump sufficient to establish pressures less than 1 Torr, e.g., 1 to 100 mTorr, e.g., 50 mTorr. The vacuum source 130 permits the chamber 110 to be maintained at a desired pressure, and permits removal of reaction byproducts and unreacted process gases.

The port 132 can be covered by a filter 134 to prevent particles thrown into the gas stream by the paddle assembly from escaping the reactor chamber 110. In addition, the system can include a filter cleaner to clear particles off the filter 134. As one example, the filter cleaner can be a mechanical knocker to strike the filter; this make shake particles off the filter. As another example, a gas source 136 (which could be provided by gas source 142e) can periodically provide a pulse of inert gas, e.g., nitrogen, into the gas line 138 between the port 132 and the vacuum source 130. The pulse of gas travels through the filter 134 back toward the chamber 110 and can blow the particles off of the filter 134. Isolation valves 139a, 139b can be used to ensure that only one of the gas source 136 or vacuum source 130 is fluidically coupled at a time to the line 138.

The chamber 110 is also coupled to a chemical delivery system 140. The chemical delivery system 140 includes multiple fluid sources 142 coupled by respective delivery tubes 143, controllable valves 144, and a fluid supply line 146. The chemical delivery system 140 delivers fluid to one or more gas injection assemblies 190 that inject the fluid in a vapor form into the chamber 110. The chemical delivery system 140 can include a combination of restrictors, gas flow controllers, pressure transducers, and ultrasonic flow meters to provide controllable flow rate of the various gasses into the chamber 110. The chemical delivery system 140 can also include one or more temperature control components, e.g., a heat exchanger, resistive heater, etc., to heat or cool the various gasses before they flow into the chamber 110.

The chemical delivery system 140 can include five fluid sources 142a, 142b, 142c, 142d, 142e. Two of the fluid sources, e.g., fluid sources 142a, 142b, can provide the two chemically different precursors or reactants for the deposition process for forming an oxide layer on the particles. For example, the first fluid source 142a can provide trimethylaluminum (TMA) or titanium tetrachloride (TiCl4), whereas the fluid gas source 142b can provide water. Another two of the fluid sources, e.g., fluid sources 142c, 142d, can provide the two chemically different precursors or reactants for the deposition process for forming a polymer material on the oxide layer. For example, the third fluid source 142c can provide adipoyl chloride, and the fourth gas source 142d can provide ethylene diamine. One of the fluid sources, e.g., the fifth fluid source 142e, can provide an inert gas, e.g., argon or $N_2$, for purging between cycles or half-cycles in the deposition process.

Although FIG. 1 illustrates five fluid sources, the use of fewer gas sources could still be compatible with deposition of an oxide or polymer layer, and use of more gas sources could enable formation of an even wider variety of laminate structures.

For one or more of the fluid sources, the chemical delivery system 140 delivers the precursor or reactant in liquid form to the gas injection assembly 190. The gas injection assembly 190 includes a vaporizer 148 to convert the liquid to vapor immediately before the precursor or reactant enters an injection manifold 194. This reduces upstream pressure loss to enable more pressure loss to occur across the particle bed 10. The more pressure loss that occurs across the particle bed 10, the lower the injection apertures can be place, and the more likely that all of the precursor will be reacted as it traverses the particle bed for a given flow rate. The vaporizer 149 can be immediately adjacent the reactor side wall, e.g., secured to or housed within the reactor wall side 112.

As shown in FIG. 1, there can be a manifold 194 for each precursor or reactant fluid, and each manifold 194 can be fluidically connected separately to the chamber 110. Thus, the precursors or reactants cannot mix until actually within the chamber 110. Alternatively, the gas lines from the fluid sources 142 could be joined as a combined fluid supply line, e.g., by a valve. The gas injection assembly 190 will be discussed further below.

As noted above, a paddle assembly 150 is positioned in the chamber 110 to agitate the particles in the particle bed. The paddle assembly 150 includes a rotatable drive shaft 152 and a plurality of paddles 154. The paddles 154 are connected to the drive shaft 152 by struts 156 that extend at outward from the drive shaft 152, such that rotation of the drive shaft 152 about an axis of rotation 153 carries the paddles 154 in a circular path (see arrow C) around the axis of rotation 153. The struts 156 can extend perpendicular to the drive shaft 152. The drive shaft 152 and axis of rotation 153 can extend along the boundary between the upper portion 110b and the lower portion 110a of the chamber 110.

The drive shaft 152 is driven by a motor 160 located outside the chamber 110. For example, the drive shaft 152 can extend through the chamber wall 112 with one end coupled to the motor 160. A bearing vacuum seal 162 can be used to seal the chamber 110 from the external environment. The other end of the drive shaft can be supported by a bearing inside the chamber 110, e.g., the end of the drive shaft 152 can fit into a recess in the inner surface of the chamber wall 112. Alternatively, the drive shaft 152 can simply be held in a cantilevered configuration with the end of the drive shaft unsupported. This can be advantageous for disassembly and cleaning. The motor 160 can rotate the drive shaft 152 and paddle assembly 150 at speeds of 0.1 to 60 rpm.

At least some of the paddles 154 are held by the struts 156 in a position such that, as the drive shaft 152 rotations, an outer edge of a paddle 154 almost contacts the interior surface 114 of the chamber wall 112. However, the outer edge of the paddle 154 remains separated from the interior surface by a small gap G1, e.g., 1 to 4 mm, e.g., 0.8 to 1.5 mm. The gap G1 can be as small as possible within manufacturing tolerances such that the paddle 154 does not scrape the outer wall 112.

The axis of rotation 153 of the drive shaft 152 can be parallel, e.g., collinear, with the center axis of the cylinder that defines the lower portion 110a. In this case, with rotation of the drive shaft 152 can cause the outer edge of a paddle 154 to sweep across the half-cylinder inner surface, e.g., across the entirety of the half-cylinder inner surface, of the lower portion 110a.

Figure 3C:
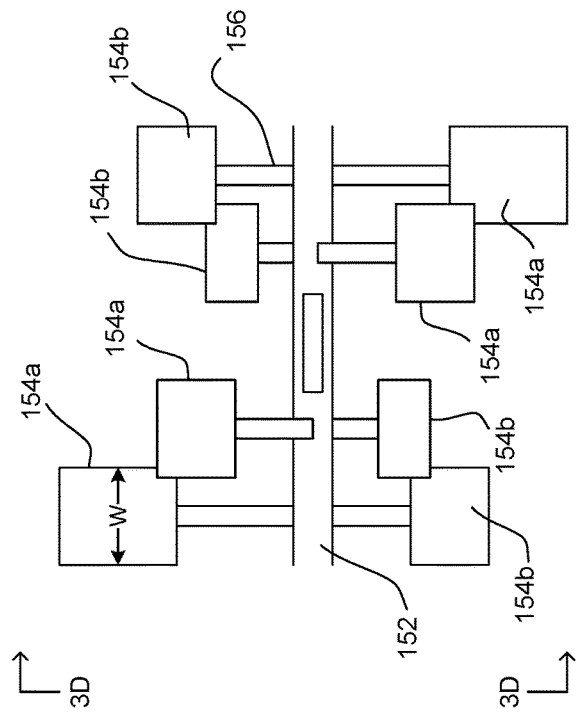
FIG. 3C is a schematic side view of another implementation of a paddle assembly.
Figure 3D:
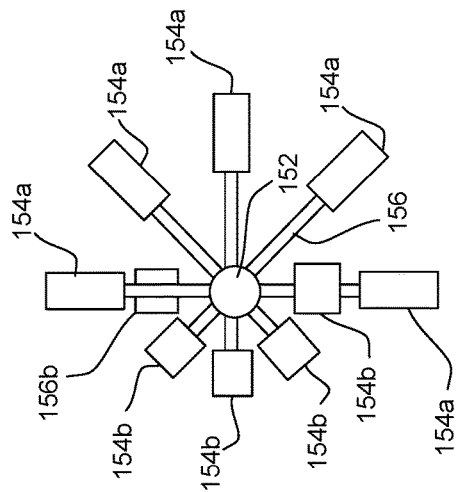
FIG. 3D is a front side view of the paddle assembly of FIG. 3C.
Figure 3A:
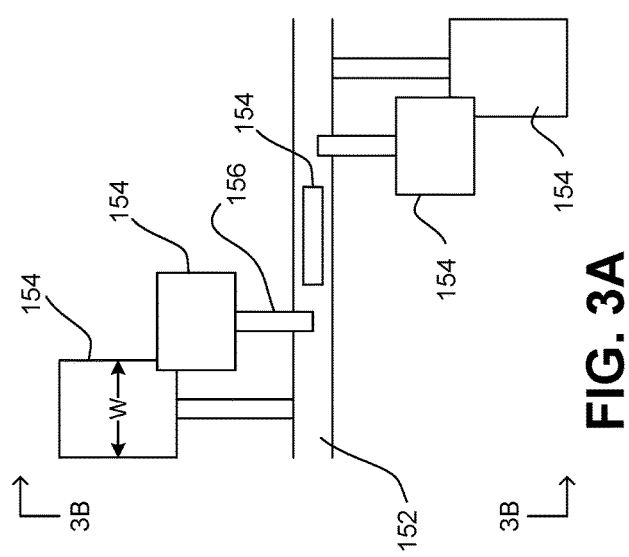
FIG. 3A is a schematic side view of a paddle assembly.
Figure 3B:
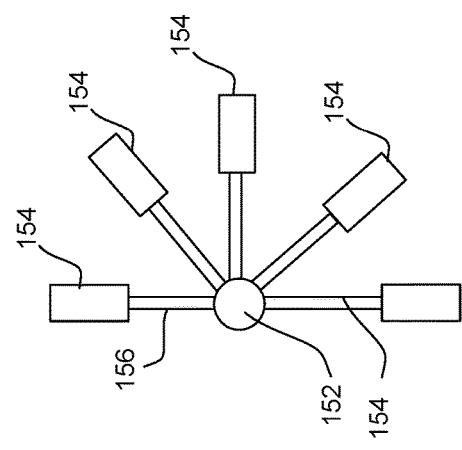
FIG. 3B is a front side view of the paddle assembly of FIG. 3A.

The paddles 154 can be spaced along the drive shaft 152 so as to ensure that the paddles that almost contact the interior surface 114 provide coverage along substantially the entire length of the reactor chamber 110. In particular, the paddles 154 be spaced and have a width W (along the axis of rotation) such that there are no gaps in the volume that is swept by the paddle assembly 150s. In particular, the width W can be greater than the pitch of the paddles along the drive shaft 152. The paddles at the different axial positions along the length of the drive shaft can be angularly offset. For example, as shown in FIGS. 3A and 3B, the paddles 154 can be arranged in a spiral pattern around the drive shaft 152. However, many other configurations are possible for the angular offsets, e.g., alternating sides of the drive shaft.

In some implementations, some of paddles 154 are positioned radially closer to the drive shaft 152 than other paddles 154. The paddles 154b that are closer to the drive shaft can be termed "inner paddles," and the paddles 154a that are farther from the drive shaft can be termed "outer paddles." The inner and outer paddles 154a, 154b can either not be overlapping radially, or can be partially overlapping radially. For example, the inner and outer paddles can overlap by at most 20% of the radial span S of the outer paddles (e.g., G≥0.8*S).

The outer paddles 154a can be spaced and have a width (along the axis of rotation) such that there are no gaps in the volume being swept by the outer paddles 154a. In particular, the widths of the outer paddles 154a can be greater than the pitch of the outer paddles 154a along the drive shaft 152. Adjacent outer paddles 154a along the length of the drive shaft can be angularly offset. Similarly, the inner paddles 154b can also be spaced and have a width (along the axis of rotation) such that there are no gaps in the volume being swept by the inner paddles 154b. In particular, the widths of the inner paddles 154b can be greater than the pitch of the inner paddles 154b along the drive shaft 152. Adjacent inner paddles 154b along the length of the drive shaft can be angularly offset. For example, as shown in FIGS. 3C and 3D, the inner paddles 154b can be arranged in a first spiral around the drive shaft 152, and the outer inner paddles 154a can be arranged in a second spiral pattern around the drive shaft 152. The spirals of the inner and outer paddles 154a, 154b are shown as 180° out of phase, but this is not required. Moreover, many other configurations are possible for the angular offsets between adjacent paddles, e.g., the paddles could be placed on alternating sides of the drive shaft.

Figure 4:
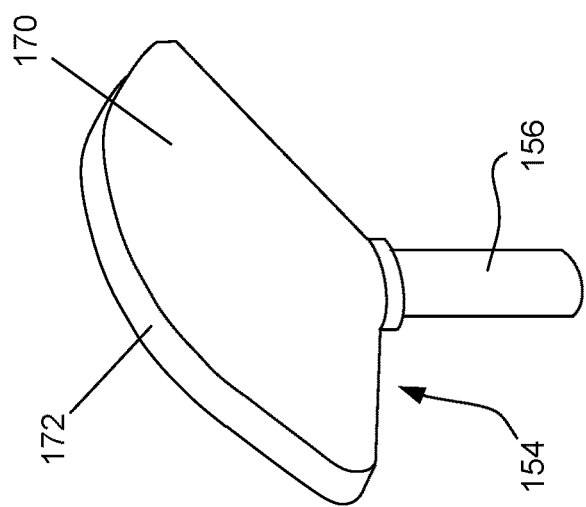
FIG. 4 is a schematic perspective view of a paddle.

Referring to FIG. 4, each paddle 154 can be a generally planar body with a primary surface 170 to push the particles in the particle bed, and a thinner edge 172 that will contact the inner surface of the lower portion 110a of the chamber 110. As shown in FIG. 4, a paddle 154 can be flared with a fan-shape. Or, as shown in FIGS. 1 and 2, a paddle can be generally rectangular, e.g., rectangular with rounded edges. The surface 170 of the paddle 154 can be flat, or the surface 170 could be concave, e.g., spoon-shaped. In addition, in some implementations the paddle 154 is plough-shaped, e.g., convex or sharply convex relative to the direction of motion of the paddle. Further discussion of paddle shape is found below with reference to FIGS. 12A and 12B.

Returning to FIG. 1, in some implementations, paddles are clustered in groups positioned in a common plane normal to the axis of rotation 153. The paddles in a group can be spaced at substantially equal angular intervals around the drive shaft 152. A group can include four paddles, although two, three or five or more paddles can be used.

Figure 5:
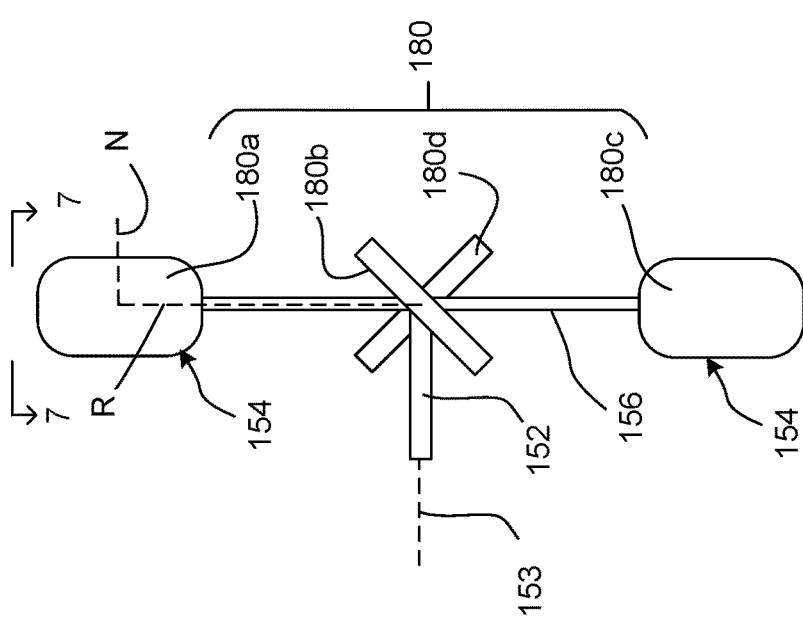
FIG. 5 is a schematic front view of a group of paddles from a paddle assembly.

For example, referring to FIGS. 1 and 5, the paddle assembly 150 includes a group 180 of four paddles 180*a*, 180*b*, 180*c*, 180*d* spaced at 90 degree angles apart and equidistant from the drive shaft 152 and axis of rotation 153. The paddles 180*a*-180*d* can be positioned to almost contact the half-cylinder inner surface of the lower portion 110*a* of the chamber 110*a*.

As shown in FIGS. 1 and 2, the paddle assembly 150 can include multiple groups of paddles that are positioned at different locations along the drive shaft 152. For example, the paddles assembly can include groups 180, 182, 184, 186, 188. Where there are three or more groups, the groups of paddles can be space at substantially equal intervals along the drive shaft 152. Each group can have the same number of paddles, e.g., four paddles. The paddles in adjacent groups can be offset angularly about the axis of rotation, e.g., by half the angle between paddles within a group. For example, if the groups have four paddles spaced 90° apart about the axis of rotation, then paddles of adjacent groups can be offset by 45°.

In some implementations, e.g., as shown in FIG. 1, the paddles in a group can be located substantially equal distances from the axis of rotation 153, e.g., the struts 156 can have the same length.

However, in some implementations, some of the paddles in a group are positioned radially closer to the drive shaft 152 than other paddles in the group. For example, the paddle assembly 150 shown in FIG. 6A includes a group of four paddles 180*a'*, 180*b'*, 180*c'*, 180*d'* spaced at 90 degree angles apart. Two of the paddles, e.g., two opposite paddles 180*a'* and 180*c'*, are located a first distance from the drive shaft 152. These two paddles can be positioned to nearly contact the half-cylindrical inner surface 112 of the lower portion 110*a*. Another two of the paddles, e.g., two opposite paddles 180*b'* and 180*d'*, are located a shorter second distance from the drive shaft 152.

As another example, the paddle assembly shown in FIG. 6B includes a group of eight paddles 180*a*-180*h* spaced at 45 degree angles apart. Four outer paddles 154*a*, e.g., paddles 180*a*-180*d*, are located a first distance from the drive shaft 152. These four outer paddles 154*a* can be positioned to nearly contact the half-cylindrical inner surface 112 of the lower portion 110*a*. Four inner paddles 154*b*, e.g., paddles 180*e*-180*h*, are located a shorter second distance from the drive shaft 152. The outer paddles 154*a* and inner paddles 154*b* are placed in an alternating arrangement around the drive shaft 152.

In some implementations, some of the groups of paddles have paddles that are positioned radially closer to the drive shaft 152 than the paddles of other groups. For example, the paddle assembly 150 includes a group 182 of four inner paddles 182*a*, 182*b*, 182*c*, 182*d* spaced at 90 degree angles apart and equidistant from the drive shaft 152 and axis of rotation 153. The outer edges of the paddles 182*a*-182*d* are spaced apart from the half-cylinder inner surface of the lower portion 110*a* of the chamber 110*a* by a gap G. The inner paddles 182*a*-182*d* are radially inward compared to the outer paddles 180*a*-180*d*.

Returning to FIGS. 1, 5 and 7, each paddle 154 can be positioned and oriented such that an axis N normal to the planar face 170 of the paddle 154 is perpendicular to the radius R passing from the axis of rotation 153 to the paddle 154. However, in some implementations, one or more paddles 154 can be angled such that orbiting of the paddle 154 about the axis of rotation 153 tends to force the particles radially toward or away from axis of rotation 153.

Figure 7:
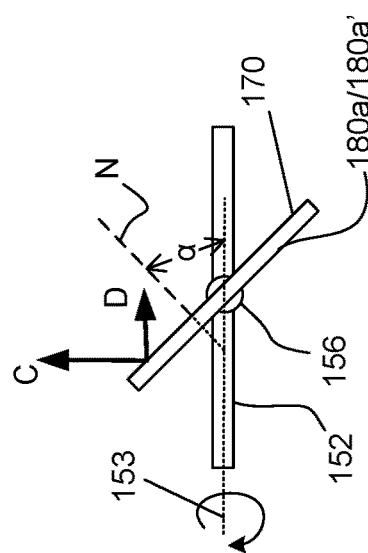
FIG. 7 is a schematic top view of a paddle from the group of paddles in FIG. 5 or 6.

In addition, each paddle 154 can be at an oblique angle relative to the plane normal to the axis of rotation 153. In particular, each paddle 154 can be angled such that orbiting of the paddle 154 about the axis of rotation 153 tends to force the particles in a direction parallel to the axis of rotation 153. For example, as shown in FIGS. 5 and 7, a paddle 180*a* is oriented such that an axis N normal to the planar face 170 of the paddle 154 is at an oblique angle α relative to the axis of rotation 153 when viewed along the radius (e.g., parallel to the strut 156) between the paddle 180*a* and the axis of rotation 153. In this configuration, when the paddle orbits about the axis of rotation 153, it will have an instantaneous vector of motion C. The oblique angle α of the paddle 180*a* will drive the powder in a direction D perpendicular to the C. The oblique angle α can be between 15-75°, e.g., be between 30-60°, e.g., be about 45°.

The inner paddles in a group can be oriented with a common oblique angle α, and the outer paddles in a group can be oriented with a common oblique angle α'. In some implementations, all the inner paddles along the drive shaft 152 are oriented with a common oblique angle α, and all the outer paddles along the drive shaft 152 are oriented with a common oblique angle α'.

The angles α' and α' are not equal. In particular, the angles α' and α' can have opposite sign. In some implementations, the angle α' is of equal magnitude but opposite sign as the angle α, e.g., the oblique angle is +a for the outer paddles and −α for the outer paddles.

In some implementations, the outer paddles 154 are angled such that orbiting of the paddles ends to force the particles in a first direction parallel to the axis of rotation 153, whereas the inner paddles 154 are angled such that orbiting of the inner paddles 154 tends to force the particles in the anti-parallel direction, i.e., a second direction opposite the first direction. For example, referring to FIGS. 6 and 7, the outer paddles 180*a'* and 180*c'* in a group 180 can force the particles in the direction D, whereas the inner paddles 180*b'* and 180*d'* in the group can force the particles in a direction opposite to D. Further discussion of the angles of the respective inner and outer paddles is found below with reference to FIGS. 11-16.

Referring to FIG. 2, in some implementations, a port 116*a* is located somewhere along, e.g., near the center of, the length of the chamber 110. The port 116*a* can be placed in the lower portion 110*a* of the chamber 110, at the bottom of the semicircular portion. The port 116*a* can be used to deliver and/or withdraw the particles from the reactor 100. In such an implementation, the outer paddles can be oriented to push the particles toward the port 116*a*, and the inner paddles can be oriented to push the particles away from the port 116*a*.

For example, the outer paddles of groups 180 and 182 can push the particles leftward toward the port 116*a*, and the inner paddles of groups 180 and 182 can push the particles rightward away from the port 116. Conversely, the outer paddles of groups 184, 186 and 188 can push the particles rightward toward the port 116*a*, and the inner paddles of groups 184, 186 and 188 can push the particles leftward away from the port 116*a*. Paddles oriented to push the particles a first direction, e.g., leftward, can be oriented with the oblique angle +α, whereas addles oriented to push the particles in an opposite second direction, e.g., rightward, can be oriented with the oblique angle −α.

If the paddles in each group have the same radial distance from the drive shaft, the paddles in different groups, e.g., adjacent groups, can have different oblique angles. For example, referring to the paddles 180a-180d in a first group 180 can force the particles in the direction D, whereas paddles 182a-182d in a second group 180 can force the particles in a direction opposite to D.

Figure 8:
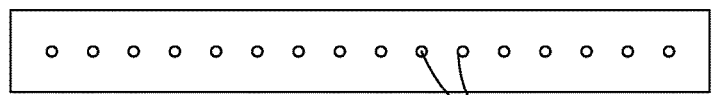
FIG. 8 is a schematic side view of gas injection ports.

Referring to FIGS. 1 and 8, the chemical delivery system 140 is coupled to the chamber 110 by a gas injection assembly 190. The gas injection assembly includes a plurality of apertures 192 that extend through the chamber wall 112. The apertures 192 can be arranged in a row, e.g., parallel to the axis of rotation 153 of the drive shaft 152. Although FIG. 8 illustrates a single row of apertures 192, the system can have multiple rows of apertures. In particular, there can be different rows of apertures for the different reactants or precursors. In addition, there can be multiples rows of apertures for a given reactant and/or precursor.

The apertures 192 are located below the expected position of the top surface 12 of the particle bed. In particular, the apertures 192 through the chamber wall 112 can be located in the lower portion 110a of the chamber 110. For example, the apertures 192 can be extend through the curved semi-circular portion of the side wall 112. The apertures 192 can be positioned in the lower half, e.g., the lower third, e.g., lower quarter, e.g., lower fifth (as measured by vertically) of the chamber wall 112 of the lower portion 110a. The apertures can have a diameter of 0.5 to 3 mm. Although FIG. 1 illustrates the apertures 192 are illustrated as extending through the chamber wall horizontally, this is not required, as explained further below.

Figure 9:
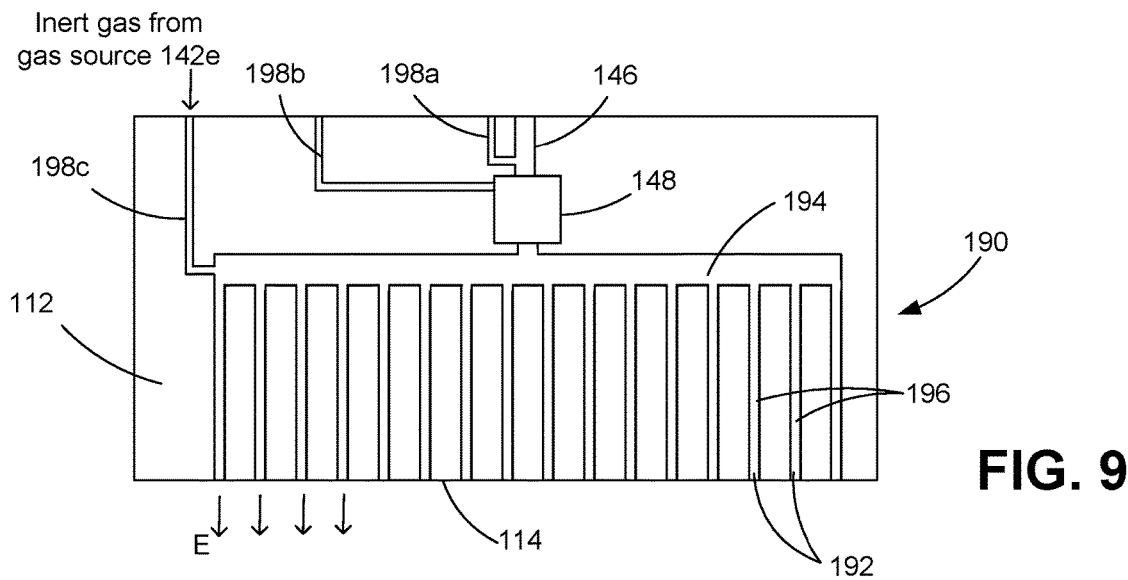
FIG. 9 is a schematic top view the gas injection ports of FIG. 8.

Referring to FIGS. 1 and 9, the gas injection assembly 190 includes a manifold 194 with multiple channels 196 leading from the manifold 194 to the apertures 192. The manifold 194 and channels 196 can be formed as passages through a solid body that provides a portion of the chamber wall 112. The vaporizer 148 can be positioned immediately upstream of the manifold 194.

An inert carrier gas, e.g., $N_2$, can flow from one of the fluid sources, e.g., the fluid source 142e, through one or more passages 198 into the manifold 194. In operation, the carrier gas can flow continuously into the manifold 194, i.e., whether or not the precursor or reactor gas is flowing into the manifold 194. As one example, the carrier gas can be injected through a passage 198a into the fluid line 146 before the liquid reaches the vaporizer. As another example, the carrier gas can be injected through a passage 198b directly into the vaporizer 148. As another example, the carrier gas can be injected through a passage 198c directly into the manifold 194.

When the precursor or reactor gas is not being injected into the chamber 110 through the manifold 194, the flow of the carrier gas can prevent back-streaming into the aperture 192 of the another precursor or reactor gas that is being injected from another manifold. The flow of carrier gas can also prevent fouling of the aperture 192, e.g., blockage of the aperture, by the particles in the particle bed 10. In addition, the carrier gas can provide the purge gas for the purge operation when the precursor or reactor gas is not being injected into the chamber 110.

The flow of carrier gas into the vaporizer 149 when the precursor gas is also flowing can improve vaporization of the precursor or reactant liquid. Without being limited by any particular theory, the carrier gas flow can assist in shearing the liquid during aerosolization, which can lead to smaller droplet size, which can be vaporized more quickly. Flow of the carrier gas into the manifold 148 when the precursor gas is also flowing can assist in drawing precursor gas out of the vaporizer.

Gas from the chemical delivery system 130, flows out of the apertures in a direction (indicated by arrow E) into the chamber 110. Assuming that the chamber 110 is partially filled with the particles, the gas is injected near a bottom of the particle bed 10. Thus, the chemicals of the gas must "bubble" through the body of the particle bed 10 to escape and be drawn out by the vacuum port 132. This can help ensure that the particles are uniformly exposed to the gas.

The direction of rotation of the paddle assembly 150 (indicated by arrow C) can such that the paddle sweeps across the apertures 192 in a direction that has a component in the same direction (i.e., no anti-parallel component) as the gas flow (indicated by arrow E). This can prevent the particles from being forced back against the gas flow and blocking the apertures 192.

Figure 10:
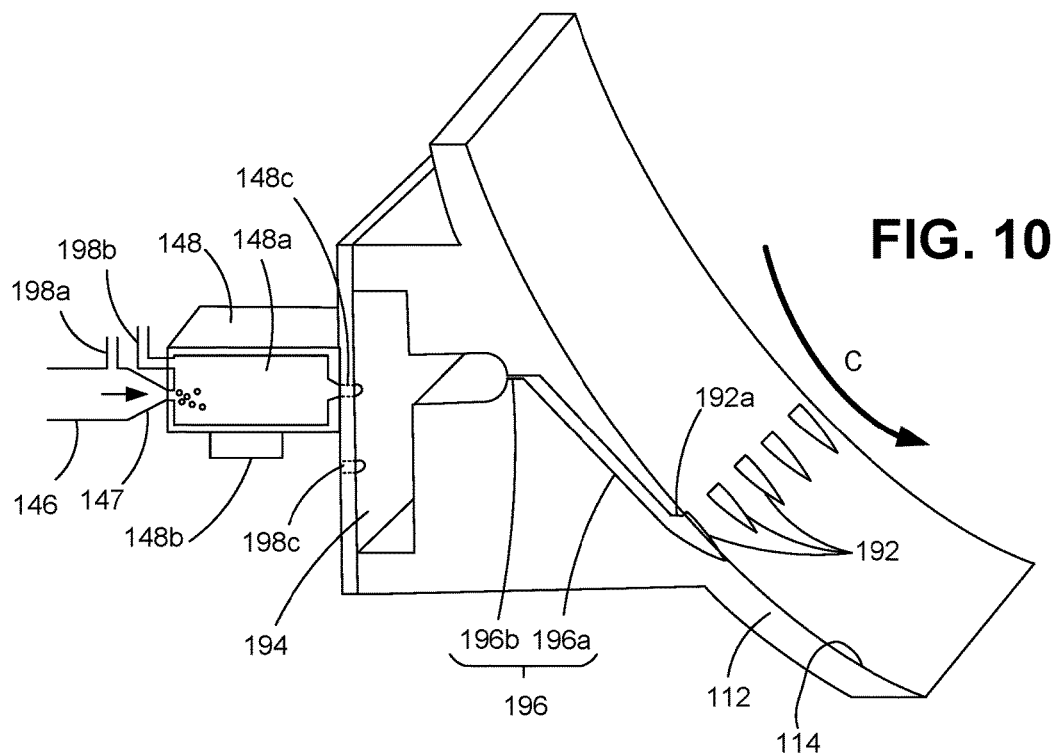
FIG. 10 is a schematic perspective view, partially cross-sectional, showing a gas injection assembly.

Referring to FIG. 10, the gas injection assembly 190 can be configured to inject gas into the chamber 110 with a direction of gas flow that is substantially parallel to the instantaneous direction of motion of the paddle 154 as it passes over the apertures 192. Stated differently, the direction of gas flow at injection can be substantially tangent to the curved inner surface 114 of the cylindrical bottom portion 110a of the chamber 110. In addition, the gas injection assembly 190 can be positioned and oriented such that the gas flow is toward the bottom of the chamber 110 (rather than toward the surface of the power bed).

Each channel 196 can include a first channel portion 196a that extends at a shallow angle toward the inner surface 114. This first channel portion 196a opens to the chamber 110 at apertures 192. As shown in FIG. 10, the apertures 192 can be scalloped recesses with a sharp indent and then a depth that gradually decreases along the direction of rotation (shown by arrow C) of the paddles 154. The first channel portion 196a can open to a ceiling 192a of the aperture 192 formed by the sharp indent. This configuration can reduce likelihood of particles from entering the channel 196. In addition, the first channel portion 196a can wider than the expected diameter of the particles. This can reduce the risk of particles clogging the first channel portion 196a.

The channel 196 also includes a second channel portion 196b that extends between the manifold 194 and the first channel portion 196a. The second channel portion 196b is narrower than the first channel portion 196a. This narrower channel portion 196b controls flow rate and flow distribution out of the manifold 194.

The vaporizer 148 can include an internal cavity 148a surround by walls that are heated by a heater 148b, e.g., a resistive heater, thermoelectric heater, heat lamp, etc. The fluid supply passage 146 is coupled to the cavity 148a by a nozzle 147. As the liquid passes through the nozzle 147, it is aerosolized. The combination of elevated temperature, rapid pressure change and high surface area of aerosol enables rapid vaporization of large quantities of the reactant or precursor. The cavity 149a of the vaporizer 148 can extend along a substantial portion, e.g., at least half, of the length of the chamber 110. The liquid reactant or precursor can be injected through the nozzle 147 at one of the cavity, and an aperture 148c for the reactant or precursor vapor to pass into the manifold 194 can be located at opposite end of the cavity chamber (along the length of the chamber 110).

As noted above, the vaporizer 148 can be integrated into the body that provides the manifold. For example, the vaporizer 148, manifold 194 and channels 196 can all be part of a single unitary body.

In some implementations, one or more temperature control components are integrated into the chamber walls 112 to permit control of the temperature of the chamber 110. For example, resistive heater, a thermoelectric cooler, a heat exchanger, or coolant flowing in cooling channels in the chamber wall, or other component in or on the side walls 112.

The reactor system 100 also includes a controller 105 coupled to the various controllable components, e.g., the vacuum source 130, the chemical delivery system 140, the motor 160, the temperature control system, etc., to control operation of the reactor system 100. The controller 105 can also be coupled to various sensors, e.g., pressure sensors, flow meters, etc., to provide closed loop control of the pressure of the gasses in the chamber 110.

In general, the controller 105 is configured to operate the reactor system 100 in accord with a "recipe." The recipe specifies an operating value for each controllable element as a function of time. For example, the recipe can specify the times during which the vacuum source 130 is to operate, the times of and flow rate for each gas source 142a-142e, the rotation rate of the drive shaft 152 as set by the motor 160, etc. The controller 105 can receive the recipe as computer-readable data (e.g., that is stored on a non-transitory computer readable medium).

The controller 105 and other computing devices part of systems described herein can be implemented in digital electronic circuitry, or in computer software, firmware, or hardware. For example, the controller can include a processor to execute a computer program as stored in a computer program product, e.g., in a non-transitory machine readable storage medium. Such a computer program (also known as a program, software, software application, or code) can be written in any form of programming language, including compiled or interpreted languages, and it can be deployed in any form, including as a standalone program or as a module, component, subroutine, or other unit suitable for use in a computing environment. In some implementations, the controller 105 is a general purpose programmable computer. In some implementations, the controller can be implemented using special purpose logic circuitry, e.g., an FPGA (field programmable gate array) or an ASIC (application specific integrated circuit).

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Convective Reactor System

As described above, when a group of paddles 180 orbits about the drive shaft 152, powder in a lower portion 110a of the stationary vacuum chamber 110 is displaced in opposing directions by the inner paddles and outer paddles. In some embodiments, the paddle assembly 150 is configured such that the volumes displaced in the opposing directions are equal.

The paddle assembly 150 can include multiple outer paddles and multiple inner paddles, extending radially from the drive shaft such that the rotation of the drive shaft by a motor orbits the multiple paddles about the drive shaft 152. The outer paddles include a first cross-section including an outer curvature and oriented at a first oblique angle and the inner paddles include a second cross-section and oriented at a second oblique angle. The first cross-section and second cross-section and first oblique angle and second oblique angle are such that orbiting of the paddles about the axis of rotation 153 of the drive shaft 152 causes the outer paddles and the inner paddles to displace equal volumes in the lower portion of the stationary vacuum chamber.

Figure 11:
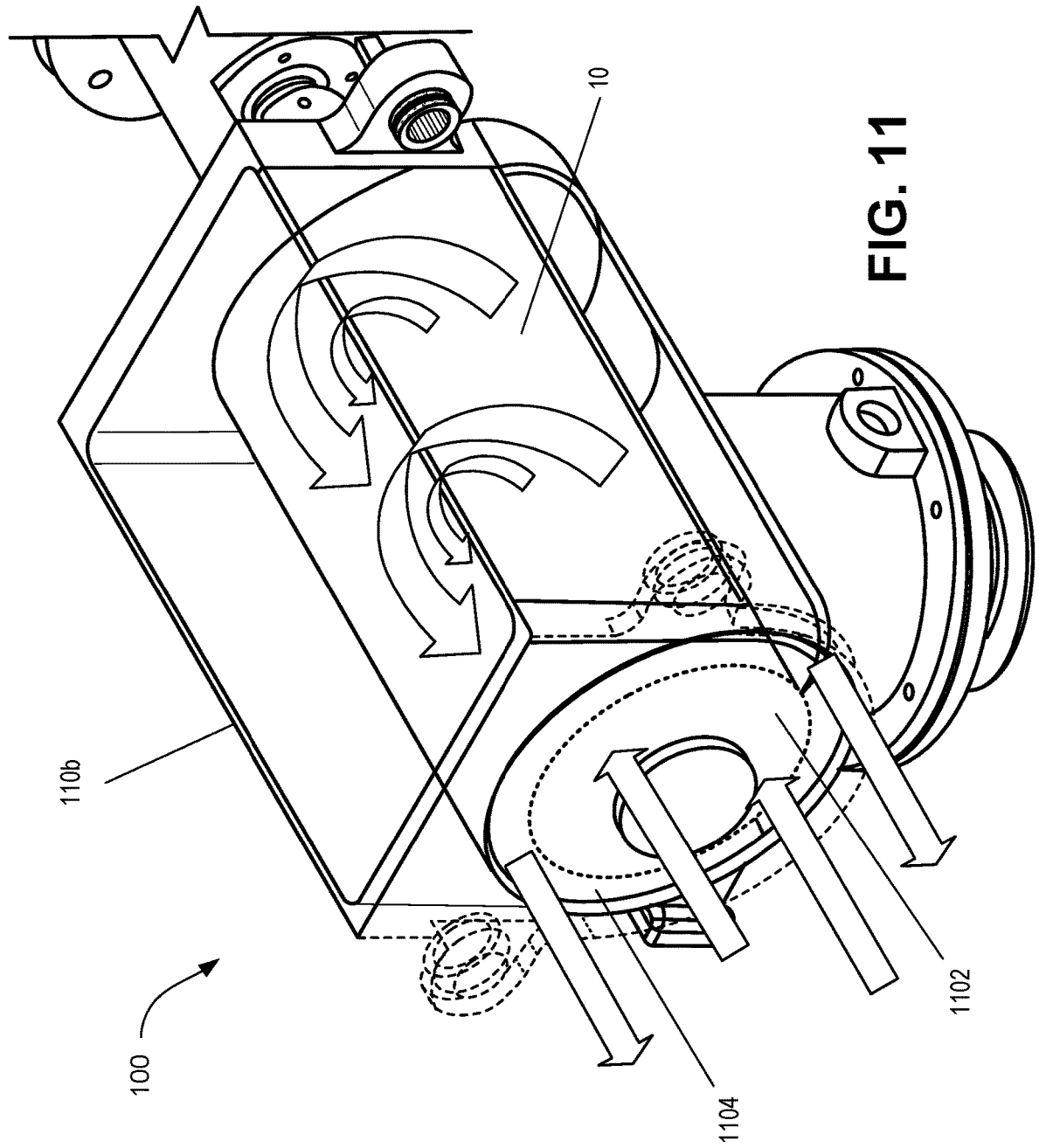
FIG. 11 is a schematic perspective partial view of a reactor.

FIG. 11 is a schematic perspective partial view of a reactor. As depicted in FIG. 11, an inner cylindrical zone 1102 and an outer cylindrical zone 1104 within the particle bed are swept in opposite directions. The inner cylindrical zone 1102, e.g., a cylindrical inner volume having an inner radius at the outer surface of the drive shaft and an outer radius at the outer rim 1214 of the inner paddles 1206, and the outer cylindrical zone 1104, e.g., a cylindrical outer volume having an inner radius at the outer rim 1214 of the inner paddles 1206 and an outer radius at the outer rim 1202 of the outer paddles 1200, are the respective volumes swept per one rotation of the paddle assembly each of the inner paddles and the outer paddles, respectively.

In one example, a volume of the inner cylindrical zone 1102 and a volume of the outer cylindrical zone 1104 is 2 to 6 liters of powder. A number of paddles for the multiple inner paddles and a number of paddles for the multiple outer paddles can be selected based on a paddle geometry, or rather, a volume swept by one paddle per rotation of the paddle assembly such that the total volume swept by the number of paddles is the same, and to minimize dead zones, i.e., volumes that paddles do not pass through and thus do not directly agitate, in the powder volume. A number of paddle geometries are contemplated. Particular paddle geometries for an outer paddle is depicted in FIG. 12A and for an inner paddle is depicted in FIG. 12B.

Figure 12A:
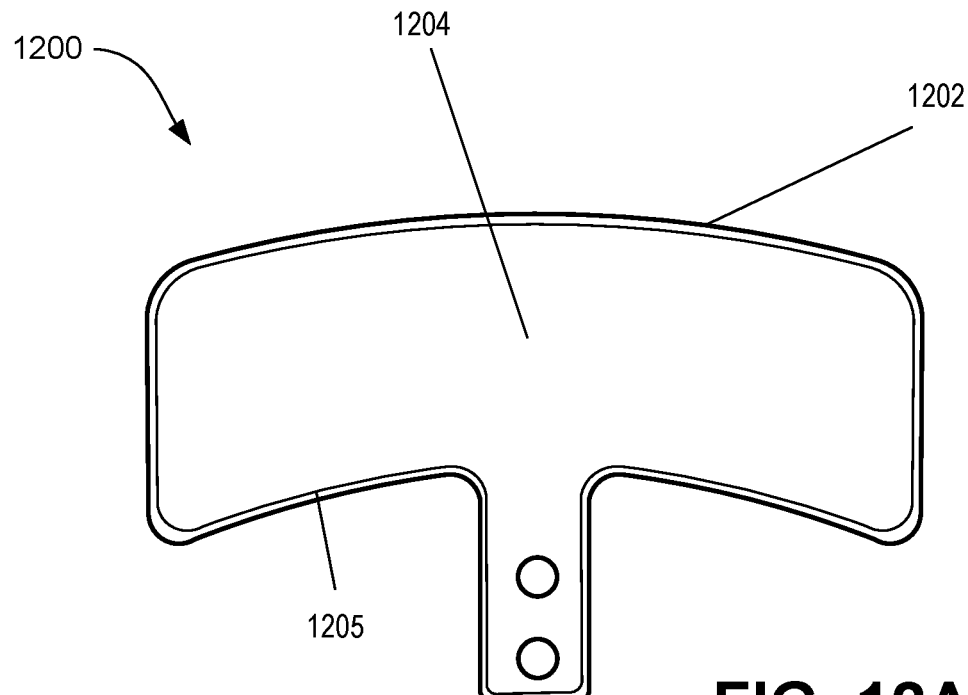
FIG. 12A is schematic top view of an outer paddle.
Figure 12B:
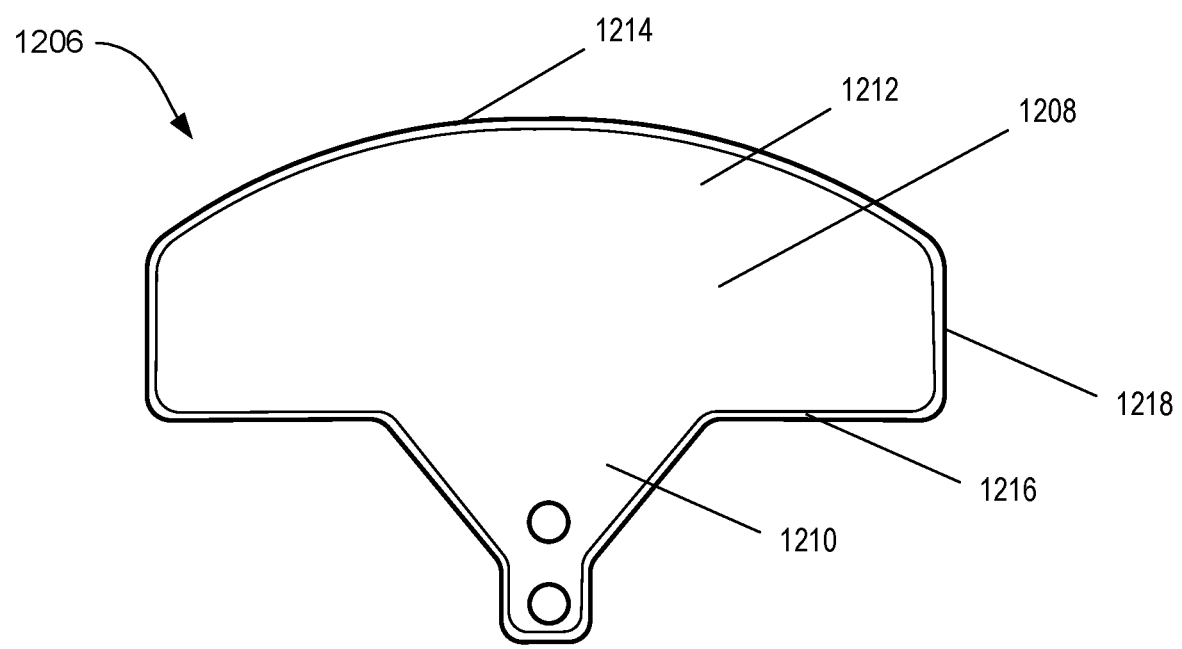
FIG. 12B is a schematic top view of an inner paddle.

FIG. 12A is schematic perspective view of an outer paddle. A curvature of an outer rim 1202 of the outer paddle 1200 is selected to conform to an interior surface 114 of a lower portion 110a of the reactor chamber 110. In some implementations, the curvature of outer rim 1202 of the first cross-section 1204 matches an inner curvature of the lower portion of the stationary vacuum chamber. The outer curvature of the cross-section 1204 of the outer paddle 1200 can depend in part on an angle at which the outer paddle is oriented on the drive shaft 152. In some implementations, the outer curvature 1202 of the cross-section 1204 of the outer paddle 1200 is parabolic.

In some implementations, a curvature of inner rim 1205 of the cross-section 1204 of the outer paddle 1200 can be concave. The curvature of inner rim 1205 can have a same or different curvature as a curvature of outer rim 1202. The inner rim 1205 can have a curvature that is concentric with the curvature of the outer rim. This can be advantageous in reduction of dead zones. In some implementations, a width of the cross-section 1204 along an axis perpendicular to the drive shaft 152 is not uniform, where the outer edges of the outer paddle 1200 can be wider than a central portion of the cross-section 1204 that is aligned with the drive shaft 152. The cross-section of the outer paddle 1200 can be symmetric across the drive shaft 152.

The outer curvature 1202 of the outer paddle 1200 can match the inner curvature of the lower portion of the stationary vacuum chamber such that, when the paddle assembly orbits the drive shaft, the outer curvatures of the outer paddles 1200 contact or nearly contact, e.g., are less than 0.8 to 1.5 mm from, the inner curvature of the lower portion 110a of the reactor chamber 110. For example, the outer rim of the of the outer paddles 1200 can be no more than 5 mm, e.g., no more than 3 mm, e.g., no more than 1 mm, from the inner surface of the lower portion 110a of the reactor chamber 110. The curvature of the outer rim 1202 of the outer paddle 1200 can be selected to substantially prevent powder adhesion to the inner reactor walls.

FIG. 12B is a schematic perspective view of an inner paddle 1206. In some implementations, a bottom portion 1210 of the inner paddle 1206 closest to an attachment point of the inner paddle 1206 to the drive shaft 154 is triangular in shape, and spans an angle that is approximately equal to 360° divided by a number of inner paddles 1206 in the paddle assembly, e.g., 360°/5 or ~72° degrees. A top portion 1212 of the inner paddle 1206 can flare outwardly, and can span an angle that is greater than 360° divided by the number of inner paddles 1206 in the paddle assembly, e.g., greater than 72° degrees.

In some implementations, a curvature of an outer rim 1214 of the inner paddle 1206 matches a curvature of the inner rim 1205 of the outer paddle 1200. The curvature of the outer rim 1214 of the inner paddle 1206 can be a convex curve.

In some implementations, a curvature of the outer rim 1214 of the inner paddle 1206 does not extend all the way to the flat portion 1216 of the lower portion 1210 of the inner paddle. As depicted in FIG. 12B, a linear section 1218 can connect the outer rim 1214 to the flat portion 1216 at approximately a right angle with respect to the flat portion 1216. The cross-section of the inner paddle 1206 can be symmetric across the drive shaft 152.

The cross-sectional area 1208 of inner paddle 1206, in particular the portion 1210 of the paddle geometry that is closest to the attachment point of the inner paddle to the drive shaft 152, substantially reduces dead zones within the inner cylindrical zone 1102 of the particle bed, e.g., reduces dead zones to at most 1.0%, e.g., at most 0.5%, e.g., 0%, of the inner cylindrical zone. In other words, the cross-sectional area of the inner paddle 1206 is such that an area is covered by a projection of the cross-sectional areas of the respective set of inner paddles is such that the set of inner paddles agitates substantially all, e.g., greater than 95%, e.g., greater than 97%, e.g., greater than 99%, e.g., 100%, of the volume of the inner cylindrical zone 1102 when the paddle assembly orbits the drive shaft 154. In some implementations, the inner cylindrical zone that is displaced by the inner paddles as the inner paddles orbit about the drive shaft includes a dead zone that is less than 5% of the inner cylindrical zone, e.g., a volume of the inner cylindrical zone 1102 that is not agitated by the set of inner paddles 1206 when the paddle assembly orbits the drive shaft 154.

Figure 6A:
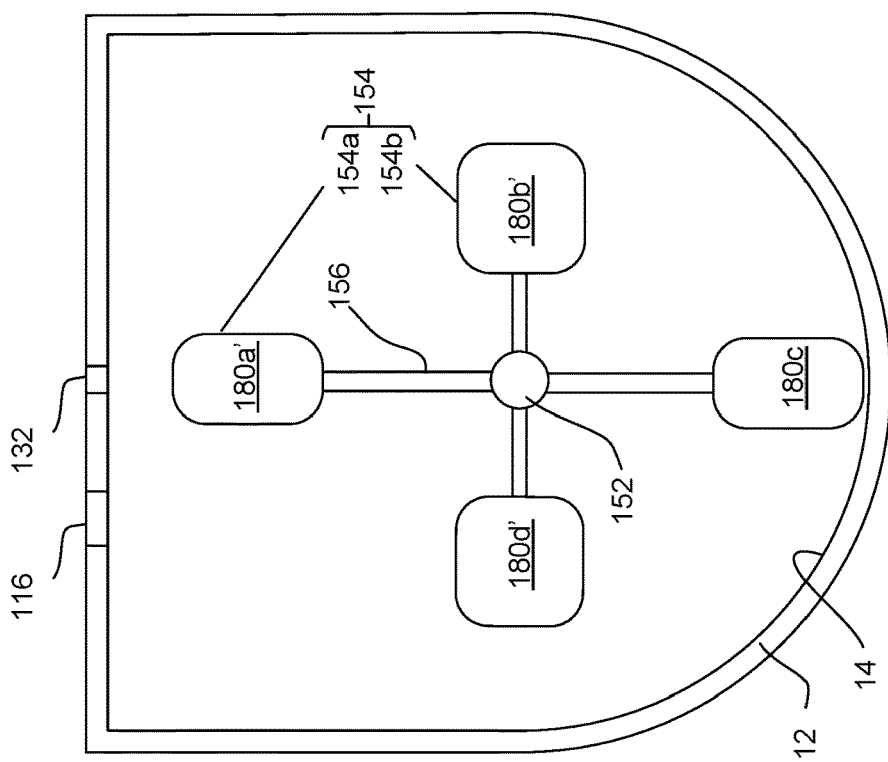
FIG. 6A is a schematic front view of another implementation of a group of paddles from a paddle assembly.

The overall configuration, e.g., the overlapping triangular cross-sections of the lower portions 1210 of the inner paddles 1206, the overlap between the outer rim 1214 of the inner paddle 1206 an the inner rim 1205 of the outer paddle 1200, and the angular spacing of the inner and outer paddles about the drive shaft so that the left edge of one paddle overlaps the right edge of another paddle (see FIG. 13) can substantially eliminate dead zones at least in the particle bed in the lower portion 110a of the chamber. For example, the dead zones in the lower portion 110a can be less than 1%, e.g., less than 0.5% of volume of the particle bed.

Where the upper portion 110c of the chamber 110 curves inwardly, e.g., as shown in FIG. 6B, dead zones can be substantially eliminated in the entire particle bed. For example, the dead zones in the particle bed can be at most 1%, e.g., at most 0.5%, e.g., 0%, of volume of the particle bed. Where the upper portion 110c of the chamber 110 curves has vertical sidewalls, e.g., as shown in FIGS. 1 and 6A, if the top surface 12 of the particle bed 10 is above the curved portion, then there may be regions near the chamber wall 112 that the paddles cannot reach. However, chamber can be filled to a level such that the dead zones in the particle bed are be at most 15%, e.g., at most 10%, e.g., at most 5%, of volume of the particle bed.

Referring back to FIG. 11, based on a particular set of inner and outer paddle geometries, a number of inner paddles 1200 and a number of outer paddles 1206 are selected such that a total volume displaced by the inner paddles, e.g., inner cylindrical zone 1102 and a total volume displaced by the outer paddles, e.g., outer cylindrical zone 1104 is equal. In the example of the outer and inner paddle geometries depicted in FIGS. 12A, 12B respectively, each outer paddle 1200 can displace a volume of X liters per one full rotation of the drive shaft 152 and each inner paddle can displace a volume of Y liters per one full rotation of the drive shaft 152. To achieve an equal volumetric displacement per one full rotation of the drive shaft, therefore, outer cylindrical zone volume/X number of outer paddles and inner cylindrical zone volume/Y number of inner paddles are arranged along the drive shaft, as depicted in FIGS. 13-15.

Figure 13:
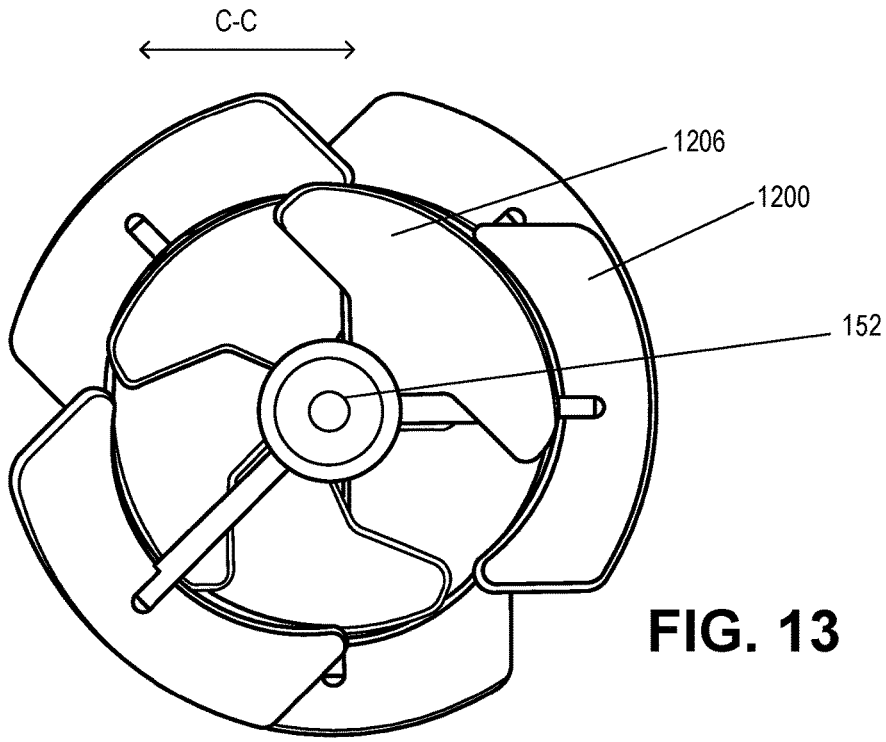
FIG. 13 is a schematic side view taken along an axis of the drive shaft of a group of paddles from a paddle assembly.

FIG. 13 is a schematic perspective view of a group of paddles from a paddle assembly taken along an axis of rotation of the drive shaft. Each inner paddle 1206 of the multiple inner paddles is oriented on the drive shaft 152 such that a portion of each inner paddle 1206 overlaps with another inner paddle along an axis C-C perpendicular to the drive shaft 152. In some implementations, a number of inner paddles and the cross-section 1208 of each inner paddle substantially avoids dead zones in the particle bed 10, e.g., powder disposed within the lower portion 110a of the stationary vacuum chamber 110 when the inner paddles orbit about the shaft axis.

Each outer paddle 1200 of the multiple outer paddles is oriented on the drive shaft 152 such that a portion of each outer paddle overlaps with another outer paddle along an axis C-C perpendicular to the drive shaft. Each inner paddle of the multiple inner paddles and each outer paddle of the multiple outer paddles is oriented on the drive shaft 152 such that a portion of each of the inner paddles overlaps with a portion of an outer paddle. In other words, each outer paddle is oriented on the drive shaft 152 such that the outer paddle has an overlap 1207a with another outer paddle, e.g., a few millimeters of overlap. In one example, overlap 1207a is 3 millimeters of overlap between a first outer paddle and a second, adjacent outer paddle on the drive shaft 152. Similarly, each inner paddle is oriented on the drive shaft 152 such that the inner paddle has an overlap 1207b with another inner paddle, e.g., a few millimeters of overlap. In one example, overlap 1207b is 3 millimeters of overlap between a first inner paddle and a second, adjacent inner paddle on the drive shaft 152

Figure 14:
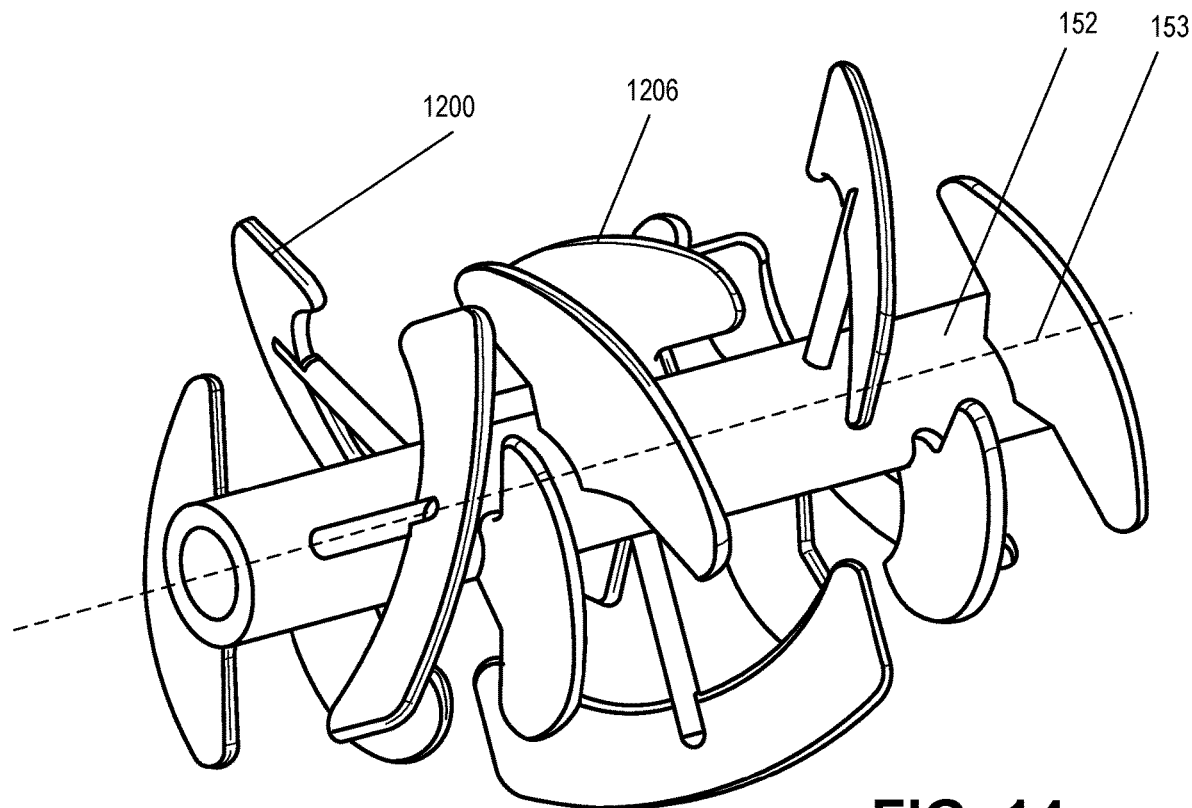
FIG. 14 is a schematic perspective view of a group of paddles from a paddle assembly.
Figure 15:
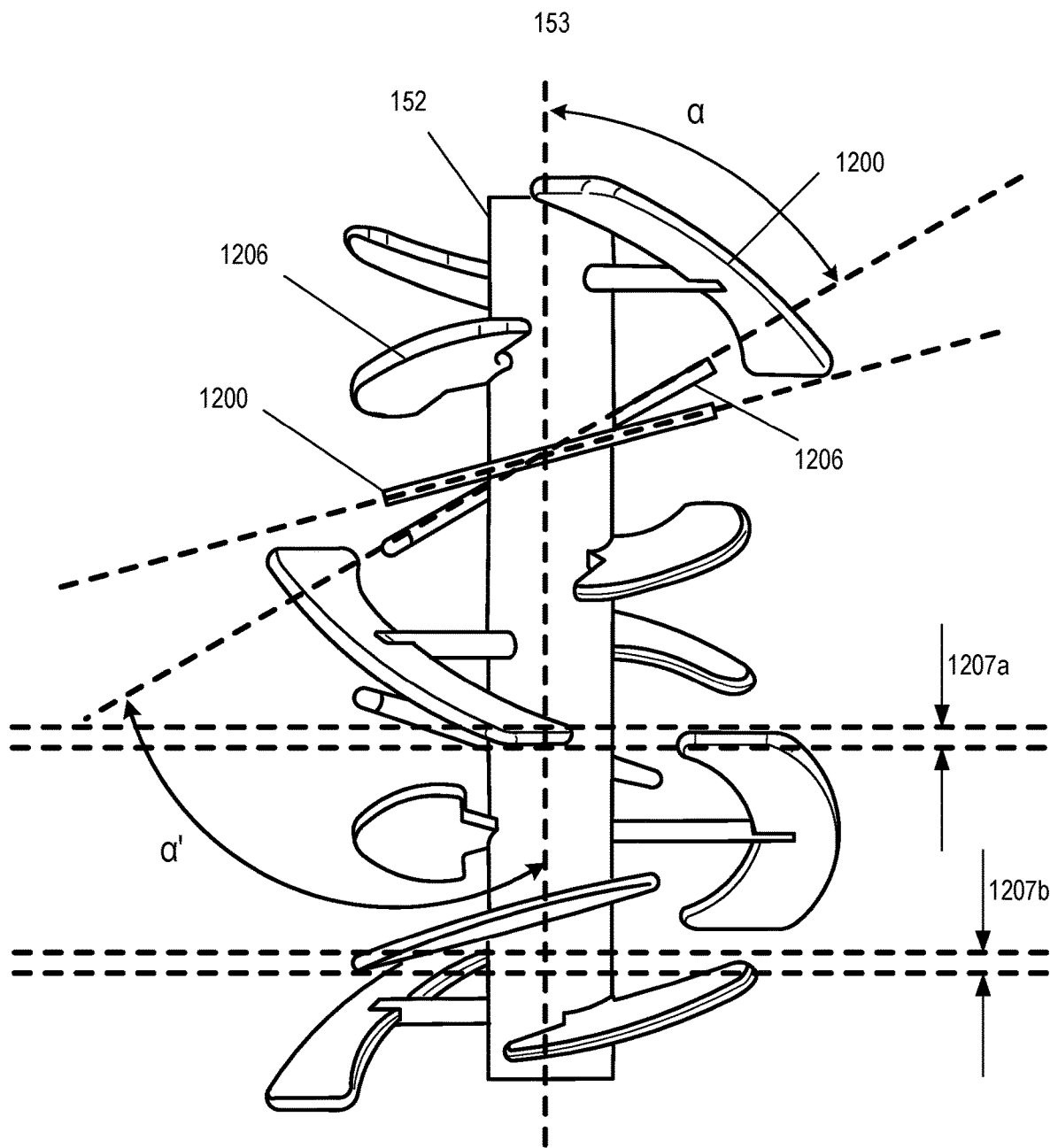
FIG. 15 is a schematic perspective top view of a group of paddles from a paddle assembly.

Moreover, each of the multiple inner paddles 1206 and multiple outer paddles 1200 is oriented on the drive shaft 152 such that, along the axis of rotation 153 of the drive shaft, the inner paddles and the outer paddles are distributed evenly along the length, as depicted in FIGS. 14 and 15.

FIG. 14 is a schematic perspective view of a group of paddles from a paddle assembly. As depicted in FIG. 14, the inner paddles 1206 and the outer paddles 1200 are both distributed along the axis of rotation 153 of the drive shaft 152.

FIG. 15 is a schematic perspective side view of a group of paddles from a paddle assembly. As depicted in FIG. 15, each of the inner paddles and each of the outer paddles is oriented at a respective angle $\alpha$ and $\alpha'$ with respect to the axis of rotation 153 of the drive shaft 152. In some implementations, the outer paddles 1200 oriented at the first oblique angle $\alpha'$ drive particles in a first direction along the axial axis 153 and the inner paddles 1206 oriented at the second oblique angle α drive particles in a second direction along the axial axis opposite to the first direction.

In some implementations, the outer paddles 1200 with first cross-section 1204 oriented at a first oblique angle α' and the inner paddles 1206 with second cross-section 1208 oriented at a second oblique angle α displace equal volumes in the lower portion of the stationary vacuum chamber when the inner paddles and the outer paddles orbit about the drive shaft 152. The equal volume displacement in opposing directions generates a convection of the particles in the particle bed. The first oblique angle α' and the first cross-section 1204, and the second oblique angle α and the second cross-section 1208 of the outer paddles and the inner paddles, respectively, i) encourage disintegration of powder aggregates and ii) limit a scooping action of the respective blades and the powder, when the paddle assembly orbits about the drive shaft 152. In one example, particle aggregates larger than five times the size of an individual particle are deaggregated as the paddles assembly orbits the drive shaft. In another example, less than 2% of the powder is scooped above the powder bed, e.g., no scooping of the particles above the particle bed by the paddles as the paddle assembly orbits about the drive shaft. In some embodiments, speed of drive shaft rotation, vacuum pressure, and/or gas flow rate within particular regimes, e.g., high flow rates, can contribute to a suspension of particles in the chamber above the particle bed, e.g., fuming of the particles.

In some implementations, the first oblique angle α' and the first cross-section 1204, and the second oblique angle α and the second cross-section 1208 of the outer paddles and the inner paddles, respectively, the first oblique angle and the first cross-section, and the second oblique angle and the second cross-section of the inner paddles and the outer paddles, respectively, minimize a bed surface angle of powder with respect to an initial powder level after a rotation of the drive shaft about the axial axis. The bed surface angle can depend in part on characteristics of the powder. In one example, the bed surface angle of powder with respect to the initial powder level after the rotation of the drive shaft about the axial axis is less than 10°, e.g., less than 5°, e.g., less than 3°, e.g., less than 1°.

A particular inner paddle angle α can be selected to be larger than a particular outer paddle angle α', for example, when a cross-section area 1208 of the inner paddle 1206 is larger than a cross-section area 1204 of the outer paddle 1200. In some implementations, inner paddle angle α and outer paddle angle α' can balance a volume of powder that is lifted above a particle bed 10 by the paddle assembly and a disintegration of the powder aggregates during an orbiting of the paddle assembly about the drive shaft 152. Additionally, inner paddles 1206 and outer paddles 1200 are oriented on the drive shaft 152 at respective angles α and α' to generate equal bulk motion of the powder in the particle bed 10 in opposing directions of the lower portion 110a of the stationary vacuum chamber 110, as described above with reference to FIG. 11. In other words, the inner and outer paddles are oriented on the drive shaft at respective angles to allow the paddles to pass through the powder volume and break up powder aggregates. In one example, each of the inner paddles 1206 is oriented at a 75 degree angle with respect to the axis of rotation 153 of the drive shaft 152, and each of the outer paddles 1200 is oriented at a 60 degree angle with respect to the rotational axis 153 of the drive shaft 152.

In some implementations, paddle geometries, oblique angle of orientation, and location of the paddles along the drive shaft axis ensures powder from the extremities of the reactor bowl make it to the intake manifold opening during the orbiting of the paddle assembly about the drive shaft, while preventing powder from entering the exhaust of the system. Paddle geometries and orientation of the paddles along the drive shaft axis can be selected in combination with flow and pressure regimes for the gas manifold system to de-aggregate powder without creating rat holes.

In some implementations, paddle geometries and orientation of paddles along the drive shaft with respect to the axis of rotation 153 are selected in combination with one or more of a drive shaft rotational speed, chamber pressure, and precursor inlet velocity.

Figure 16:
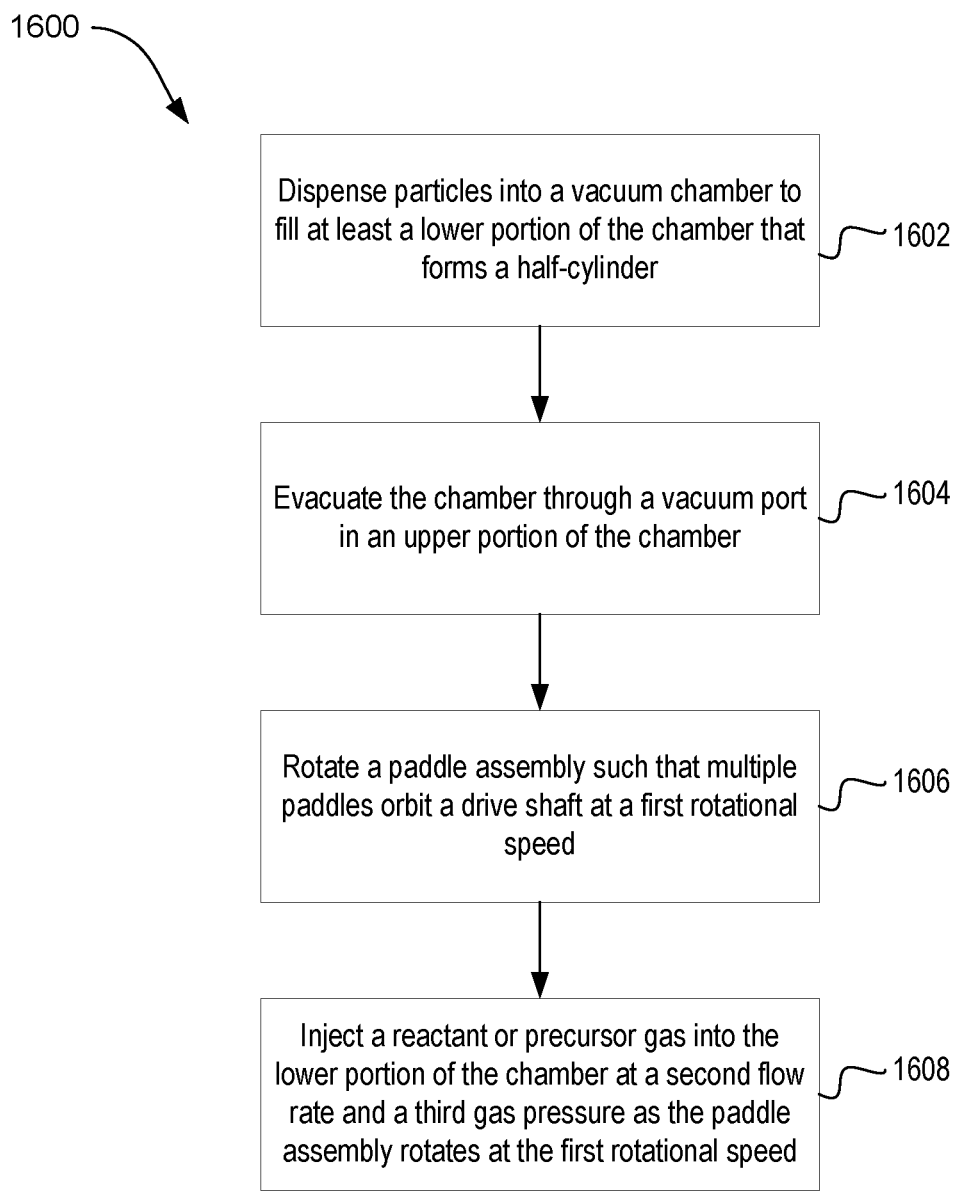
FIG. 16 is a flow diagram of an example process of the reactor that includes a stationary drum.

FIG. 16 is a flow diagram of an example process 1600 of the reactor system that includes a stationary vacuum chamber. In a first step, particles 10 are dispensed into the stationary vacuum chamber 110 to fill at least a lower portion 110a of the stationary vacuum chamber 110 that forms a half-cylinder (1602). In some embodiments, the particles are dispensed via a powder delivery port 116a, as depicted in FIG. 2.

The chamber is evacuated through a vacuum port in an upper portion of the chamber (1604). The vacuum chamber 110 can be evacuated through a vacuum port 132 by a vacuum source 130, e.g., one or more vacuum pumps, that is located in an upper portion 110b of the chamber 110.

A paddle assembly is rotated such that multiple paddles orbit a drive shaft at a first rotational speed (1606). Paddle assembly 150 includes multiple paddles, e.g., paddles 180a-h, paddles 1200, paddles 1206, etc., orbiting a drive shaft 152 at a first rotational speed. The multiple paddles can include multiple inner paddles 1206 and multiple outer paddles 1200 oriented at respective oblique angles α and α' along the rotational axis 153 of the drive shaft 152. Orbiting the drive shaft 152 about the rotational axis 153 causes the multiple paddles to displace a volume of powder within a particle bed 10. In some implementations, a first volume of powder, e.g., inner cylindrical zone 1102, is displaced by the rotation of the inner paddles 1206 and a second volume of powder, e.g., outer cylindrical zone 1104, is displaced by the rotation of the outer paddles 1200, where the first volume and the second volume are equal.

A reactant or precursor gas is injected into the lower portion of the vacuum chamber at a second flow rate and a third gas pressure as the paddles assembly rotates at the first rotational speed (1608). A reactant or precursor gas can be injected by an injection manifold 194 into the lower portion 110a of the vacuum chamber 110 at a flow rate and gas pressure as the drive shaft rotates about the axis of rotation 153. In one example, the drive shaft is rotated at a speed of 60 RPM counter-clockwise and clockwise, a flow rate of gas, e.g., nitrogen gas, is 1000 sccm, and a gas pressure is 20 Torr within the vacuum chamber 110.

In some embodiments, the drive shaft is rotated in alternating directions between counter-clockwise and clockwise, where a direction of rotation is changed, for example, every 5 to 15 minutes. In one example, a direction of rotation of the drive shaft is reversed every 5 minutes.

Operation

Initially, particles are loaded into the chamber 110 in the reactor system 100. The particles can have a solid core comprising a drug, e.g., one of the drugs discussed above. The solid core can optionally also include an excipient. Once any access ports are sealed, the controller 105 operates the reactor system 100 according to the recipe in order to form the thin-film oxide layers and/or thin polymer layers on the particles.

In operation, the reactor system 100 performs an ALD and/or an MLD thin-film coating process by introducing gaseous precursors of the coating into the chamber 110. The gaseous precursors are spiked alternatively into the reactor chamber 110. This permits the deposition process to be a solvent-free process. The half-reactions of the deposition process are self-limiting, which can provide Angstrom or nanometer level control of deposition. In addition, the ALD and/or MLD reaction can be performed at low temperature conditions, such as below 50° C., e.g., below 35° C.

Suitable reactants for ALD methods include any of or a combination of the following: monomer vapor, metal-organics, metal halides, oxidants, such as ozone or water vapor, and polymer or nanoparticle aerosol (dry or wet). For example, the first fluid source 142a can provide gaseous trimethylaluminum (TMA) or titanium tetrachloride (TiCl4), whereas the second gas source 142b can provide water. For MLD methods, as an example, the fluid source 142c can provide adipoyl chloride, and the fourth fluid 142d can provide vaporous or gaseous ethylene diamine.

In operation, one of the gasses flows from the chemical delivery system 140 into the particle bed 10 in the lower portion 110a of the chamber 110 as the paddle assembly 150 rotates. Rotation of the paddle assembly 150 agitates the particles to keep them separate, ensuring a large surface area of the particles remains exposed. This permits fast, uniform interaction of the particle surface with the process gas.

For both an ALD process and an MLD process, two reactant gases are alternately supplied to the chamber 110, with each step of supplying a reactant gas followed by a purge cycle in which the inert gas is supplied to the chamber 110 to force out the reactant gas and by-products used in the prior step.

As noted above, the coating process can be performed at low processing temperature, e.g., below 50° C., e.g., at or below 35° C. In particular, the particles can remain or be maintained at such temperatures during all of steps (i)-(ix) noted above. In general, the temperature of the interior of the reactor chamber does not exceed 35° C. during of steps (i)-(ix). This can be achieved by having the first reactant gas, second reactant gas and inert gas be injected into the chamber at such temperatures during the respective cycles. In addition, physical components of the chamber of the chamber can remain or be maintained at such temperatures, e.g., using a cooling system, e.g., a thermoelectric cooler, if necessary.

In some implementations, the controller can cause the reactor system 100 to first deposit an oxide layer on the drug-containing particles, and then deposit a polymer layer over the oxide layer on the particles, e.g., using the process described above. In some implementations, the controller can cause the reactor system 100 alternate between depositing an oxide layer and depositing a polymer layer on the drug-containing particles, so as to form a multi-layer structure with layers of alternating composition.

Continuous Flow Operation

For an ALD process, the controller 105 can operate the reactor system 100 as follows.

In a first reactant half-cycle, while the motor 160 rotates the paddle wheel 150 to agitate the particles:
  i) The gas distribution system 140 is operated to flow the first reactant gas, e.g., TMA, from the source 142a into the chamber 110 until the particle bed 10 is saturated with the first reactant gas. For example, the first reactant gas can flow at a specified flow rate and for a specified period of time, or until a sensor measures a specified first pressure or partial pressure of the first reactant gas in the upper portion 110b of the chamber. In some implementations, the first reactant gas is mixed with an inert gas as it flows into the chamber. The specified pressure or partial pressure can be 0.1 Torr to half of the saturation pressure of the reactant gas.
  ii) Flow of the first reactant gas is halted, and the vacuum source 140 evacuates the chamber 110, e.g., down to pressures below 1 Torr, e.g., to 1 to 100 mTorr, e.g., 50 mTorr.

These steps (i)-(ii) can be repeated a number of times set by the recipe, e.g., two to ten times.

Next, in a first purge cycle, while the motor 160 rotates the paddle wheel 150 to agitate the particles:
  iii) The gas distribution system 140 is operated to flow only inert gas, e.g., $N_2$, from the source 142e into the chamber 110. The inert gas can flow at a specified flow rate and for a specified period of time, or until a sensor measures a specified second pressure of the inert gas in the upper portion 110b of the chamber. The second specified pressure can be 1 to 100 Torr.
  iv) The vacuum pump 140 evacuates the chamber 110, e.g., down to pressures below 1 Torr, e.g., to 1 to 500 mTorr, e.g., 50 mTorr.

These steps (iii)-(iv) can be repeated a number of times set by the recipe, e.g., six to twenty times.

In a second reactant half-cycle, while the motor 160 rotates the paddle assembly 150 to agitate the particles:
  v) The gas distribution system 30 is operated to flow the second reactant gas, e.g., $H_2O$, from the source 142b into the chamber 110 until the particle bed 10 is saturated with the second reactant gas. Again, the second reactant gas can flow at a specified flow rate and for a specified period of time, or until a sensor measures a specified third pressure or partial pressure of the second reactant gas in the upper portion 110b of the chamber. In some implementations, the second reactant gas is mixed with an inert gas as it flows into the chamber. The third pressure can be 0.1 Torr to half of the saturation pressure of the second reactant gas.
  vi) The vacuum pump 140 evacuates the chamber 110, e.g., down to pressures below 1 Torr, e.g., to 1 to 500 mTorr, e.g., 50 mTorr.

These steps (v)-(vi) can be repeated a number of times set by the recipe, e.g., two to ten times.

Next, a second purge cycle is performed. This second purge cycle with steps (vii) and (vii) can be identical to the first purge cycle, or can have a different number of repetitions of the steps (iii)-(iv) and/or different specified pressure.

The cycle of the first reactant half-cycle, first purge cycle, second reactant half cycle and second purge cycle can be repeated a number of times set by the recipe, e.g., one to ten times.

The operation is discussed above with an ALD process, but the operation is similar for MLD. In particular, in steps (i) and (v), the reactant gasses are substituted with appropriate process gasses and pressures for deposition of a polymer layer. For example, step (i) can use vaporous or gaseous adipoyl chloride, and step (v) can use are vaporous ethylene diamine.

Moreover, although operation is discussed above with an ALD or MLD process, the system could be used for a chemical vapor deposition (CVD) process. In this case, both reactants are flowed simultaneously into the chamber 110 so as to react inside the chamber, e.g., during step (i). The second reactant half-cycle can be omitted.

Pulsed Flow Operation

In another implementation, one or more of the gases (e.g., the reactant gases and/or the inert gas) can be supplied in pulses in which the chamber 110 is filled with the gas to a specified pressure, a delay time is permitted to pass, and the chamber is evacuated by the vacuum source 140 before the next pulse commences.

In particular, for an ALD process, the controller 105 can operate the reactor system 100 as follows.

In a first reactant half-cycle, while the motor 160 rotates the paddle wheel 150 to agitate the particles:
  i) The gas distribution system 140 is operated to flow the first reactant gas, e.g., TMA, from the source 142*a* into the chamber 110 until a first specified pressure is achieved in the upper portion 110*b* of the chamber. The specified pressure can be 0.1 Torr to half of the saturation pressure of the reactant gas.
  ii) Flow of the first reactant gas is halted, and a specified delay time is permitted to pass, e.g., as measured by a timer in the controller. This permits the first reactant to flow through the particle bed 10 in the chamber 110 and react with the surface of the particles.
  iii) The vacuum pump 140 evacuates the chamber 110, e.g., down to pressures below 1 Torr, e.g., to 1 to 100 mTorr, e.g., 50 mTorr.

These steps (i)-(iii) can be repeated a number of times set by the recipe, e.g., two to ten times.

Next, in a first purge cycle, while the motor 160 rotates the paddle wheel 150 to agitate the particles:
  iv) The gas distribution system 140 is operated to flow the inert gas, e.g., $N_2$, from the source 142*e* into the chamber 110 until a second specified pressure is achieved. The second specified pressure can be 1 to 100 Torr.
  v) Flow of the inert gas is halted, and a specified delay time is permitted to pass, e.g., as measured by the timer in the controller. This permits the inert gas to diffuse through the particles in the particle bed 10 to displace the reactant gas and any vaporous by-products.
  vi) The vacuum pump 140 evacuates the chamber 110, e.g., down to pressures below 1 Torr, e.g., to 1 to 500 mTorr, e.g., 50 mTorr.

These steps (iv)-(vi) can be repeated a number of times set by the recipe, e.g., six to twenty times.

In a second reactant half-cycle, while the motor 160 rotates the paddle assembly 150 to agitate the particles:
  vii) The gas distribution system 30 is operated to flow the second reactant gas, e.g., $H_2O$, from the source 142*b* into the chamber 110 until a third specified pressure is achieved. The third pressure can be 0.1 Torr to half of the saturation pressure of the reactant gas.
  viii) Flow of the second reactant gas is halted, and a specified delay time is permitted to pass, e.g., as measured by the timer in the controller. This permits the second reactant gas to flow through the particle bed 10 and react with the surface of the particles inside the drum chamber 110.
  ix) The vacuum pump 140 evacuates the chamber 110, e.g., down to pressures below 1 Torr, e.g., to 1 to 500 mTorr, e.g., 50 mTorr.

These steps (vii)-(ix) can be repeated a number of times set by the recipe, e.g., two to ten times.

Next, a second purge cycle is performed. This second purge cycle can be identical to the first purge cycle, or can have a different number of repetitions of the steps (iv)-(vi) and/or different delay time and/or different pressure.

The cycle of the first reactant half-cycle, first purge cycle, second reactant half cycle and second purge cycle can be repeated a number of times set by the recipe, e.g., one to ten times.

Moreover, one or more of the gases (e.g., the reactant gases and/or the inert gas) can be supplied in pulses in which the chamber 110 is filled with the gas to a specified pressure, a delay time is permitted to pass, and the chamber is evacuated by the vacuum source 140 before the next pulse commences.

The operation is discussed above with an ALD process, but the operation is similar for MLD. In particular, in steps (i) and (vii), the reactant gasses are substituted with appropriate process gasses and pressures for deposition of a polymer layer. For example, step (i) can use vaporous or gaseous adipoyl chloride, and step (vii) can use are vaporous ethylene diamine.

Moreover, although operation is discussed above with an ALD or MLD process, the system could be used for a chemical vapor deposition (CVD) process. In this case, both reactants are flowed simultaneously into the chamber 110 so as to react inside the chamber, e.g., during step (i). The second reactant half-cycle can be omitted.

Use of Gas Flow for De-Agglomeration

As discussed above, even with the agitation of the particles by paddles, the particles can still form micro-agglomerates, e.g., clumps of several particles or groups forming agglomerates of up to 10× the primary particle size.

However, one or more of the gases (e.g., the reactant gases and/or the inert gas) can be injected in a manner to cause de-agglomeration of the particles in the particle bed in the chamber 110. Such an approach enables this de-agglomeration to occur in-situ, e.g., during the purge step between reactant gas exposures, thus improving process throughput and improving yield by eliminating the vacuum break and atmospheric exposure that can occur with the ex-situ process of de-agglomeration.

A related issue is overall management of gas-particle interaction. During delivery of a reactant gas to the chamber for deposition, it is desirable for the reactant gas to be moving slowly to provide the process gas with as long a residence time within the powder as possible, while still sufficiently quickly to prevent particles from back-streaming into the manifold. If the velocity of the reactant gas is too high, the reactant gas will not have time or exposure to react, and can create rat holes.

De agglomeration can be performed by the reactant gas, the purge gas, or both.

Assuming that the purge gas, i.e., the inert gas, is to be used for de-agglomeration, the gas needs to be fast enough to perform de-agglomeration, but not so fast that "rat holes" are formed through the particle bed. The paddle rotation rate can be combined with higher velocity purge gas to reduce rat-holing with jet de-aggregation. In addition, the gas flow needs to be sufficiently slow that powder stays in the particle bed rather than being "blown" out of the particle bed and into the exhaust system. Assuming that the reactant gas is to be used for de-agglomeration, it would be subject to the constraints for the inert gas and the additional constraints noted above for deposition.

The specific flow and pressure regimes will depend on particle size and composition, degree of agitation by the paddles.

During processing steps with the reactive gas, the chamber can be maintained at pressure of 1-100 Torr, e.g., to 20-50 Torr, and the flow velocity of the reactive gas (or mixture of reactive gas and inert gas) can be under 10 m/s, e.g., 1-10 m/s. In some implementations these speeds, e.g., less than 10 m/s, can be sufficient to provide de-agglomeration by the reactive gas (or mixture of reactive gas and inert gas) during the deposition step.

In some implementations, during purging steps with the inert gas, the purge gas flows into the processing chamber at the same velocity, e.g., 1-10 m/s, as the gas flow in the deposition step. In some implementations, the purge gas flows into the processing chamber at a higher velocity than in the deposition step, but still less than 10 m/s. In some implementations, the flow velocity can be increased to 30-200 m/s, e.g., 50-100 m/s. Such a velocity is sufficient to break micro-aggregates, but not enough to break the primary particles. Velocities can be kept below the supersonic velocity range of a jet mill, e.g., less than 340 m/s. In some implementations, the velocity of the purge gas is increased for a portion of the purge step, e.g., to above 30 m/s, but is kept at a lower velocity, e.g., less than 10 m/s or the same velocity as in the deposition step, for a remainder of the purge step.

The chamber pressure can be set during the purge step to a pressure below that maintained for the deposition step, e.g., less than 20 Torr, e.g., 1-20 Torr.

In some implementations, the de-agglomeration is temporary, e.g., the particles can re-agglomerate before a subsequent deposition. However, over the course of multiple deposition cycles, by breaking up micro-agglomerates so that new contact points are formed during re-agglomeration, the entirety of the particles should still be coated. In some implementations, the de-agglomeration lasts sufficiently long for a concurrent or subsequent deposition step to effectively coat an entirety of the particles, but the particles re-agglomerate by the time the particles are removed from the chamber.

CONCLUSION

The present disclosure provides apparatus for and methods of preparing pharmaceutical compositions comprising API containing particles encapsulated by one or more layers of oxide and/or one or more layers of a polymer. The coating layers are conformal and of controlled thickness from several nanometers to several micrometers in total. The articles to be coated can be composed of only API or a combination of API and one or more excipients. The coating process described herein can provide an API with an increased glass transition temperature for the API relative to uncoated API, a decreased rate of crystallization for an amorphous form of the API relative to uncoated API, and decreased surface mobility of API molecules in the particle compared to uncoated API. Importantly, particle dissolution can be altered. Because the coating is relatively thin, drug products with high drug loading can be achieved. Finally, there are benefits with respect to cost and ease of manufacture because multiple coatings can be applied in the same reactor.

Terms of relative positioning are used to refer to relative positioning of components within the system or orientation of components during operation; it should be understood that the reactor system could be held in a vertical orientation or some other orientation during shipping, assembly, etc.

A number of embodiments of the invention have been described. Nevertheless, it will be understood that various modifications may be made without departing from the spirit and scope of the invention.

What is claimed is:

1. A reactor for coating particles, comprising:
a stationary vacuum chamber to hold a bed of particles to be coated, the chamber having a lower portion that forms a half-cylinder and an upper portion;
a vacuum port in the upper portion of the chamber;
a chemical delivery system including a fluid passage through an aperture in a wall of the chamber to a deliver a precursor or reactant gas and a purge gas into the lower portion of the chamber, the aperture being located in the lower portion of the chamber; and
a paddle assembly including
a rotatable drive shaft extending through the chamber along an axial axis of the half cylinder,
a plurality of paddles, including a first plurality of outer paddles and a second plurality of inner paddles, extending radially from the drive shaft such that the rotation of the drive shaft by a motor orbits the plurality of paddles about the drive shaft, wherein
the first plurality of outer paddles comprise a first cross-section including an outer curvature and oriented at a first oblique angle,
the second plurality of inner paddles comprise a second cross-section and oriented at a second oblique angle, and
wherein the first cross-section and second cross-section and first oblique angle and second oblique angle are such that orbiting of the paddles causes the first plurality of outer paddles to sweep through and displace a first volume in the lower portion of the stationary vacuum chamber and the second plurality of inner paddles to sweep through and displace a second volume in the lower portion of the stationary vacuum chamber, and the first and second volumes are substantially equal.

2. The reactor of claim 1, wherein the outer curvature of the first cross-section matches an inner curvature of the lower portion of the stationary vacuum chamber.

3. The reactor of claim 2, wherein the outer curvature of the first cross-section is parabolic.

4. The reactor of claim 2, wherein a spacing between the outer curvature of the first plurality of outer paddles and the inner curvature of the lower portion of the stationary vacuum chamber is less than 1.5 millimeters.

5. The reactor of claim 1, wherein the second plurality of inner paddles are positioned and oriented such that orbiting of the second plurality of inner paddles results in no dead zone in the bed of particles in the lower portion of the stationary vacuum chamber.

6. The reactor of claim 5, wherein a number of inner paddles of the second plurality of inner paddles and the second cross-section of each inner paddle result in dead zones in the bed of particles of less than 5% of the lower portion of the stationary vacuum chamber when the second plurality of inner paddles orbit about the axial axis.

7. The reactor of claim 1, wherein the first plurality of outer paddles oriented at the first oblique angle drives particles in a first direction along the axial axis and the second plurality of inner paddles oriented at the second oblique angle drives particles in a second direction along the axial axis opposite to the first direction.

8. The reactor of claim 7, wherein the first oblique angle and the second oblique angle and the first cross-section and second cross-section are each displace a same volume in the lower portion of the stationary vacuum chamber when the second plurality of inner paddles and first plurality of outer paddles orbit about the drive shaft.

9. The reactor of claim 8, wherein the first oblique angle and the first cross-section, and the second oblique angle and the second cross-section of the second plurality of inner paddles and first plurality of outer paddles, respectively, results in no scooping action by respective paddles of the plurality of paddles when the plurality of paddles orbit about the drive shaft.

10. The reactor of claim 8, wherein the first oblique angle and the first cross-section, and the second oblique angle and the second cross-section of the second plurality of inner paddles and first plurality of outer paddles, respectively results in a change in a bed surface angle of the bed of particles with respect to an initial level of less than 2 degrees after a rotation of the drive shaft about the axial axis.

11. The reactor of claim 1, wherein at least a first portion of a first cross-sectional area of each of the first plurality of outer paddles overlaps with at least a second portion of a second cross-sectional area of each of the second plurality of inner paddles along the axial axis.

12. The reactor of claim 11, wherein a third portion of each outer paddle of the first plurality of outer paddles overlaps with a fourth portion of another outer paddle perpendicular to the axial axis.

13. The reactor of claim 12, wherein a fifth portion of each inner paddle of the second plurality of inner paddles overlaps with a sixth portion of another inner paddle of the second plurality of inner paddles perpendicular to the axial axis.

14. The reactor of claim 13, wherein the plurality of paddles are positioned and oriented such that orbiting of the plurality of paddles results in a dead zone in the lower portion of the chamber of less than 5% of the lower portion.

15. The reactor of claim 13, wherein the plurality of paddles are positioned and oriented such that orbiting of the plurality of paddles results in a dead zone in the lower portion of the chamber of less than 3% of the lower portion.

16. The reactor of claim 13, wherein the plurality of paddles are positioned and oriented such that orbiting of the plurality of paddles results in a dead zone in the lower portion of the chamber of less than 1% of the lower portion.

17. A reactor for coating particles, comprising:
a stationary vacuum chamber to hold a bed of particles to be coated, the chamber having a lower portion that forms a half-cylinder and an upper portion;
a vacuum port in the upper portion of the chamber;
a chemical delivery system including a fluid passage through an aperture in a wall of the chamber to a deliver a precursor or reactant gas and a purge gas into the lower portion of the chamber, the aperture being located in the lower portion of the chamber; and
a paddle assembly including
a rotatable drive shaft extending through the chamber along an axial axis of the half cylinder,
a plurality of paddles, including a first plurality of outer paddles and a second plurality of inner paddles, extending radially from the drive shaft such that the rotation of the drive shaft by a motor orbits the plurality of paddles about the drive shaft, wherein
the first plurality of outer paddles comprise a first cross-section including an outer curvature and oriented at a first oblique angle,
the second plurality of inner paddles comprise a second cross-section and oriented at a second oblique angle, and
wherein the first cross-section and second cross-section and first oblique angle and second oblique angle and a spacing of paddles about the drive shaft substantially eliminates a dead zone from the lower portion of the chamber.

* * * * *